US008772291B2

(12) United States Patent
Barbosa et al.

(10) Patent No.: US 8,772,291 B2
(45) Date of Patent: *Jul. 8, 2014

(54) MULTICYCLIC COMPOUNDS AND METHODS OF THEIR USE

(75) Inventors: Joseph Barbosa, Lambertville, NJ (US);
Li Dong, Lawrenceville, NJ (US);
Cynthia Anne Fink, Lebanon, NJ (US);
Jiancheng Wang, Plainsboro, NJ (US);
G. Gregory Zipp, Robbinsville, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 586 days.

This patent is subject to a terminal disclaimer.

(21) Appl. No.: 12/633,453

(22) Filed: Dec. 8, 2009

(65) Prior Publication Data

US 2010/0081691 A1   Apr. 1, 2010

Related U.S. Application Data

(63) Continuation of application No. 11/433,057, filed on May 12, 2006, now abandoned.

(60) Provisional application No. 60/680,501, filed on May 13, 2005.

(51) Int. Cl.
| *A01N 43/64* | (2006.01) |
| *A61K 31/53* | (2006.01) |
| *A61K 31/497* | (2006.01) |
| *A01N 43/54* | (2006.01) |
| *C07D 239/42* | (2006.01) |
| *C07D 401/04* | (2006.01) |
| *A01N 43/40* | (2006.01) |
| *A61K 31/445* | (2006.01) |
| *C07D 253/00* | (2006.01) |
| *C07D 401/00* | (2006.01) |
| *C07D 403/00* | (2006.01) |
| *C07D 409/00* | (2006.01) |
| *C07D 405/00* | (2006.01) |
| *C07D 239/00* | (2006.01) |
| *C07D 239/02* | (2006.01) |
| *C07D 241/00* | (2006.01) |
| *C07D 241/02* | (2006.01) |
| *C07D 211/20* | (2006.01) |

(52) U.S. Cl.
USPC ........ 514/242; 514/252.1; 514/256; 514/330; 544/182; 544/238; 544/242; 544/336; 546/237

(58) Field of Classification Search
USPC ............. 514/317, 242, 252.1, 256, 330; 546/192, 237; 544/182, 238, 242, 336
See application file for complete search history.

(56) References Cited

U.S. PATENT DOCUMENTS

| 5,580,775 | A  | 12/1996 | Fremeau, Jr. et al. |
| 5,759,788 | A  | 6/1998 | Fremeau, Jr. et al. |
| 6,313,127 | B1 | 11/2001 | Waterson et al. |
| 6,630,497 | B2 | 10/2003 | Reitz et al. |
| 6,645,957 | B2 | 11/2003 | Ishiwata et al. |
| 7,208,497 | B2 | 4/2007 | Dorwald et al. |
| 7,342,115 | B2 | 3/2008 | Hutchison et al. |

OTHER PUBLICATIONS

Crump et al., 1999, "Localization of the Brain-Specified High-Affinity L-Proline Transporter in Cultured Hippocampal Neurons: Molecular Heterogeneity of Synaptic Terminals", Molecular and Cellular Neuroscience 13:25-39.
Fremeau, Jr. et al., 1992, "Molecular Cloning and Expression of a High Affinity L-Proline Transporter Expressed in Putative Glutamatergic Pathways of Rat Brain", Neuron 8:915-926.
Fremeau, Jr., et al., 1996, "A Novel Nonoploid Action of Enkaphalins: Competitive Inhibition of the Mammalian Brain High Affinity L-Proline Transporter", Molecular Pharmacology 49:1033-1041.
Galli et al., 1999, "L-Profile and L-Pipecolate Induce Enkephalin-Sensitive Currents in Human Embryonic Kidney 293 Cells Transfected with the High-Affinity Mammalian Brain L-Proline Transporter", Journal of Neuroscience 19(15):6290-6297.
Renick et al., 1999, "The Mammalian Brain High-Affinity L-Proline Transporter is Enriched Preferentially in Synaptic Vesicles in a Subpopulation of Excitatory Nerve Terminals in Rat Forebrain", Journal of Neuroscience 19(1):21-33.
Shafqat, et al., 1995, "Human Brain-Specific L-Proline Transporter: Molecular Cloning, Functional Expression, and Chromosomal Localization of the Gene in Human and Mouse Genomes", Molecular Pharmacology 48:219-229.
Chemical Abstracts RN 875579-04-7, Chemical Abstracts Service, retrieved on Jul. 14, 2006.
Chemical Abstracts RN 547703-94-6, Chemical Abstracts Service, retrieved on Jul. 14, 2006.
Chemical Abstracts RN 414686-33-2, Chemical Abstracts Service, retrieved on Jul. 14, 2006.
Chemical Abstracts RN 414876-56-5, Chemical Abstracts Service, retrieved on Jul. 14, 2006.
Chemical Abstracts RN 332146-64-2, Chemical Abstracts Service, retrieved on Jul. 14, 2006.

*Primary Examiner* — Sarah Pihonak
(74) *Attorney, Agent, or Firm* — Max Bachrach

(57) ABSTRACT

This invention relates to multicyclic compounds, pharmaceutical compositions comprising them, and methods of their use in, for example, the treatment of cognitive disorders.

18 Claims, 3 Drawing Sheets

MULTICYCLIC COMPOUNDS AND METHODS OF THEIR USE

This is a continuation of application Ser. No. 11/433,057, filed May 12, 2006, which claim priority to U.S. provisional application No. 60/680,501, filed May 13, 2005, the entireties of which are incorporated herein by reference.

1. FIELD OF THE INVENTION

This invention relates to multicyclic compounds, pharmaceutical compositions comprising them, and methods of their use.

2. BACKGROUND OF THE INVENTION

The amino acid L-proline reportedly plays a role in regulating synaptic transmission in the mammalian brain. See, e.g., Crump et al., *Molecular and Cellular Neuroscience*, 13: 25-29 (1999). For example, a synaptosomal bisynthetic pathway of L-proline from ornithine has been reported, and high affinity $Na^+$-dependent synaptosomal uptake of L-proline has been observed. Yoneda et al., *Brain Res.*, 239: 479-488 (1982); Balcar et al., *Brain Res.*, 102: 143-151 (1976).

In general, neurotransmitter systems typically have mechanisms that inactivate signaling, many of which work through the action of a $Na^+$-dependent transporter. In this case, a $Na^+$-dependent transporter for proline has been described, and the molecular entity cloned (SLC6A7 in humans). See, e.g., U.S. Pat. Nos. 5,580,775 and 5,759,788. But the transporter's specific role remains unknown. For example, the human $Na^+$-dependent proline transporter is generally localized to synaptic terminals, which is consistent with a role in neurotransmitter signaling. But no high-affinity receptor has been found for proline, suggesting that it is a neuromodulator rather than a neurotransmitter. Shafqat S., et al., *Molecular Pharmacology* 48:219-229 (1995).

The fact that the $Na^+$-dependent proline transporter is expressed in the dorsal root ganglion has led some to suggest that it may be involved in nociception, and that compounds which inhibit the transporter may be used to treat pain. See, e.g., U.S. Patent Application No. 20030152970A1. But this suggestion is not supported by experimental data.

3. SUMMARY OF THE INVENTION

This invention encompasses multicyclic compounds, pharmaceutical compositions comprising them, and methods of their use. One embodiment of the invention encompasses a compound of formula I:

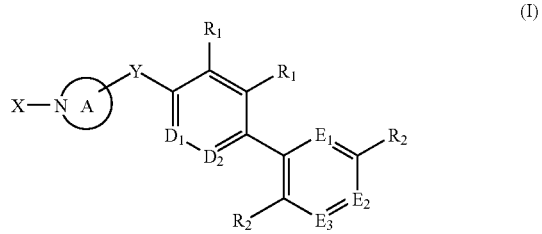

and pharmaceutically acceptable salts and solvates thereof, wherein: A is an optionally substituted non-aromatic heterocycle; each of $D_1$ and $D_2$ is independently N or $CR_1$; each of $E_1$, $E_2$ and $E_3$ is independently N or $CR_2$; X is optionally substituted heteroaryl; Y is O, C(O), CH(OH), or $CH_2$; each $R_1$ is independently hydrogen, halogen, cyano, $R_A$, $OR_A$, $C(O)R_A$, $C(O)OR_A$, $C(O)N(R_A R_B)$, $N(R_A R_B)$, or $SO_2R_A$; each $R_2$ is independently hydrogen, halogen, cyano, $R_A$, $OR_A$, $C(O)R_A$, $C(O)OR_A$, $C(O)N(R_A R_B)$, $N(R_A R_B)$, or $SO_2R_A$; each $R_A$ is independently hydrogen or optionally substituted alkyl, aryl, arylalkyl, alkylaryl, heterocycle, heterocycle-alkyl, or alkyl-heterocycle; and each $R_B$ is independently hydrogen or optionally substituted alkyl, aryl, arylalkyl, alkylaryl, heterocycle, heterocycle-alkyl, or alkyl-heterocycle.

Preferred compounds inhibit the proline transporter, and particular compounds do so without substantially affecting the dopamine or glycine transporters.

Another embodiment of the invention encompasses pharmaceutical compositions of the various compounds described herein.

Another embodiment encompasses methods of improving cognitive performance, and of treating, managing and/or preventing various diseases and disorders, using compounds of the invention.

4. BRIEF DESCRIPTION OF THE FIGURES

Certain aspects of the invention may be understood with reference to the attached figures.

5. DETAILED DESCRIPTION OF THE INVENTION

Figure 1:
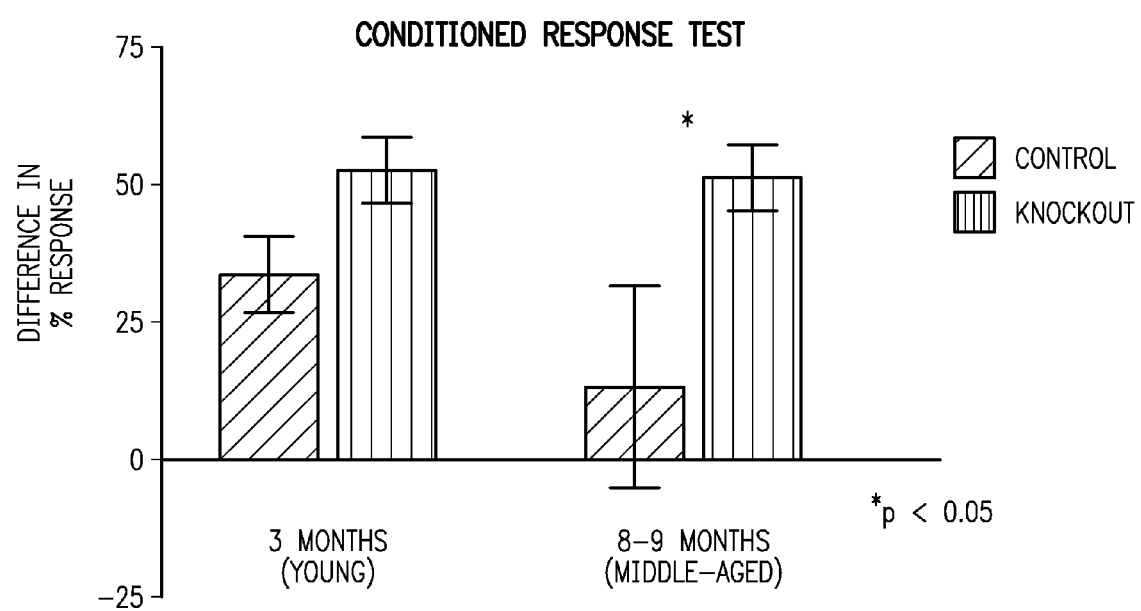
FIG. 1 shows differences between wildtype and SLC6A7-knockout mice in a conditioned response test.

This invention is based, in part, on the discovery that the proline transporter encoded by the human gene at map location 5q31-q32 (SLC6A7 gene; GENBANK accession no. NM_014228) can be a potent modulator of mental performance in mammals. In particular, it has been found that genetically engineered mice that do not express a functional product of the murine ortholog of the SLC6A7 gene display significantly increased cognitive function, attention span, learning, and memory relative to control animals. It is believed that this is the first report of experimental data tying inhibition of the proline transporter to a beneficial pharmacological effect.

In view of this discovery, the protein product associated with the SLC6A7 coding region was used to discover compounds that may improve cognitive performance and may be useful in the treatment, prevention and/or management of diseases and disorders such as Alzheimer's disease, autism, cognitive disorders, dementia, learning disorders, and short- and long-term memory loss.

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the term "DTIC$_{50}$" means an IC$_{50}$ against human recombinant dopamine transporter as determined using the assay described in the Examples, below.

Unless otherwise indicated, the term "GTIC$_{50}$" means an IC$_{50}$ for human recombinant glycine transporter as determined using the assay described in the Examples, below.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, the term "PTIC$_{50}$" means an IC$_{50}$ for human recombinant Na$^+$-dependent proline transporter as determined using the assay described in the Examples, below.

Unless otherwise indicated, the term "specific proline transporter inhibitor" means a compound that has a PTIC$_{50}$ of less than about 200 nM.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkyl-NHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NH-CONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder or one or more of its symptoms, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alkyl, aryl, or heteroaryl" has the same meaning as "optionally substituted alkyl, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more chiral centers, but which do not indicate stereochemistry (e.g., with bolded or dashed lines), encompasses pure stereoisomers and mixtures (e.g., racemic mixtures) thereof. Similarly, names of compounds having one or more chiral centers that do not specify the stereochemistry of those centers encompass pure stereoisomers and mixtures thereof.

5.2. Compounds of the Invention

This invention encompasses compounds of formula I:

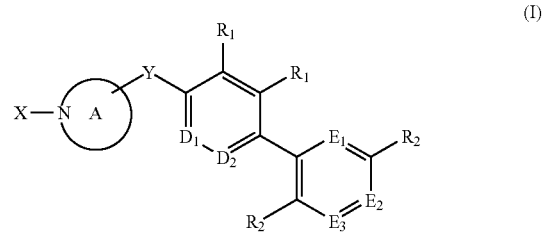

(I)

and pharmaceutically acceptable salts and solvates thereof, wherein: A is an optionally substituted non-aromatic heterocycle; each of $D_1$ and $D_2$ is independently N or CR$_1$; each of $E_1$, $E_2$ and $E_3$ is independently N or CR$_2$; X is optionally substituted heteroaryl; Y is O, C(O), CH(OH), or CH$_2$; each R$_1$ is independently hydrogen, halogen, cyano, R$_A$, OR$_A$, C(O)R$_A$, C(O)OR$_A$, C(O)N(R$_A$R$_B$), N(R$_A$R$_B$), or SO$_2$R$_A$; each R$_2$ is independently hydrogen, halogen, cyano, R$_A$, OR$_A$, C(O)R$_A$, C(O)OR$_A$, C(O)N(R$_A$R$_B$), N(R$_A$R$_B$), or SO$_2$R$_A$; each R$_A$ is independently hydrogen or optionally substituted alkyl, aryl, arylalkyl, alkylaryl, heterocycle, heterocyclealkyl, or alkyl-heterocycle; and each R$_B$ is independently hydrogen or optionally substituted alkyl, aryl, arylalkyl, alkylaryl, heterocycle, heterocycle-alkyl, or alkyl-heterocycle.

One embodiment of the invention encompasses compounds of formula IA:

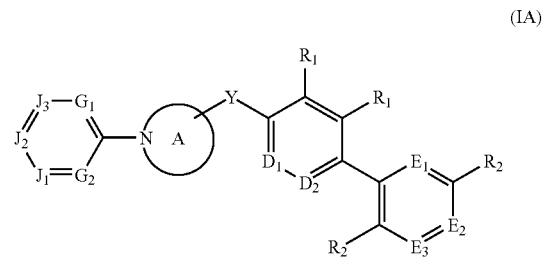

(IA)

and pharmaceutically acceptable salts and solvates thereof.

Another encompasses compounds of formula IB:

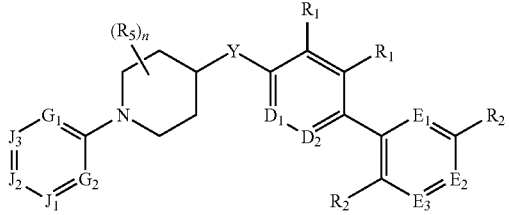

(IB)

and pharmaceutically acceptable salts and solvates thereof, wherein: each $R_5$ is independently halogen, cyano, $R_{5A}$, $OR_{5A}$, $C(O)R_{5A}$, $C(O)OR_{5A}$, $C(O)N(R_{5A}R_{5B})$, $N(R_{5A}R_{5B})$, or $SO_2R_{5A}$; each $R_{5A}$ is independently hydrogen or optionally substituted alkyl, aryl, arylalkyl, alkylaryl, heterocycle, heterocycle-alkyl, or alkyl-heterocycle; each $R_{5B}$ is independently hydrogen or optionally substituted alkyl, aryl, arylalkyl, alkylaryl, heterocycle, heterocycle-alkyl, or alkyl-heterocycle; and n is 0-5.

Another encompasses compounds of formula IC:

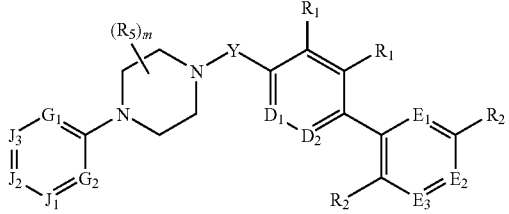

(IC)

and pharmaceutically acceptable salts and solvates thereof, wherein: Y is O, C(O) or $CH_2$; each $R_5$ is independently halogen, cyano, $R_{5A}$, $OR_{5A}$, $C(O)R_{5A}$, $C(O)OR_{5A}$, $C(O)N(R_{5A}R_{5B})$, $N(R_{5A}R_{5B})$, or $SO_2R_{5A}$; each $R_{5A}$ is independently hydrogen or optionally substituted alkyl, aryl, arylalkyl, alkylaryl, heterocycle, heterocycle-alkyl, or alkyl-heterocycle; each $R_{5B}$ is independently hydrogen or optionally substituted alkyl, aryl, arylalkyl, alkylaryl, heterocycle, heterocycle-alkyl, or alkyl-heterocycle; and m is 0-4.

Another encompasses compounds of formula ID:

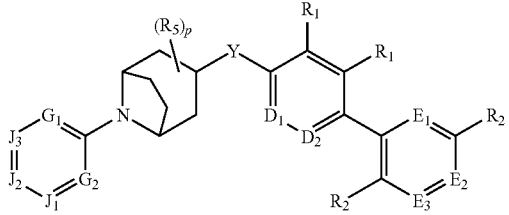

(ID)

and pharmaceutically acceptable salts and solvates thereof, wherein: each $R_5$ is independently halogen, cyano, $R_{5A}$, $OR_{5A}$, $C(O)R_{5A}$, $C(O)OR_{5A}$, $C(O)N(R_{5A}R_{5B})$, $N(R_{5A}R_{5B})$, or $SO_2R_{5A}$; each $R_{5A}$ is independently hydrogen or optionally substituted alkyl, aryl, arylalkyl, alkylaryl, heterocycle, heterocycle-alkyl, or alkyl-heterocycle; each $R_{5B}$ is independently hydrogen or optionally substituted alkyl, aryl, arylalkyl, alkylaryl, heterocycle, heterocycle-alkyl, or alkyl-heterocycle; and p is 0-7.

Another encompasses compounds of formula IE:

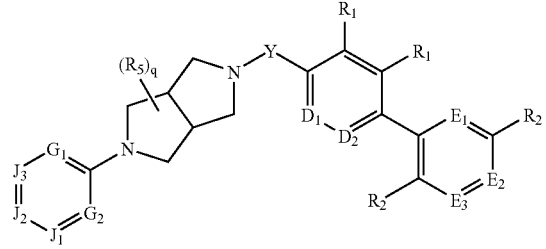

(IE)

and pharmaceutically acceptable salts and solvates thereof, wherein: Y is O, C(O) or $CH_2$; each $R_5$ is independently halogen, cyano, $R_{5A}$, $OR_{5A}$, $C(O)R_{5A}$, $C(O)OR_{5A}$, $C(O)N(R_{5A}R_{5B})$, $N(R_{5A}R_{5B})$, or $SO_2R_{5A}$; each $R_{5A}$ is independently hydrogen or optionally substituted alkyl, aryl, arylalkyl, alkylaryl, heterocycle, heterocycle-alkyl, or alkyl-heterocycle; each $R_{5B}$ is independently hydrogen or optionally substituted alkyl, aryl, arylalkyl, alkylaryl, heterocycle, heterocycle-alkyl, or alkyl-heterocycle; and q is 0-6.

Another encompasses compounds of formula IF:

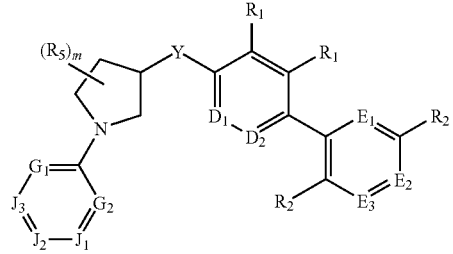

(IF)

and pharmaceutically acceptable salts and solvates thereof, wherein: each $R_5$ is independently halogen, cyano, $R_{5A}$, $OR_{5A}$, $C(O)R_{5A}$, $C(O)OR_{5A}$, $C(O)N(R_{5A}R_{5B})$, $N(R_{5A}R_{5B})$, or $SO_2R_{5A}$; each $R_{5A}$ is independently hydrogen or optionally substituted alkyl, aryl, arylalkyl, alkylaryl, heterocycle, heterocycle-alkyl, or alkyl-heterocycle; each $R_{5B}$ is independently hydrogen or optionally substituted alkyl, aryl, arylalkyl, alkylaryl, heterocycle, heterocycle-alkyl, or alkyl-heterocycle; and m is 0-4.

Another encompasses compounds of formula II:

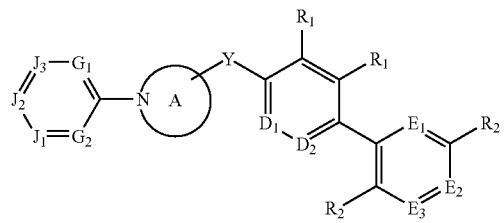

(II)

and pharmaceutically acceptable salts and solvates thereof, wherein: A is an optionally substituted non-aromatic heterocycle; each of $D_1$ and $D_2$ is independently N or $CR_1$; each of $E_1$, $E_2$ and $E_3$ is independently N or $CR_2$; each of $G_1$ and $G_2$ are independently N or $CR_3$; each of $J_1$, $J_2$ and $J_3$ are independently N or $CR_4$; Y is O, C(O), CH(OH), or $CH_2$; each $R_1$ is independently hydrogen, halogen, or $(C_{1-10})$alkyl; each $R_2$ is independently halogen, cyano, $R_{2A}$, $OR_{2A}$, or $SO_2R_{2A}$; each $R_{2A}$ is independently hydrogen or $(C_{1-10})$alkyl optionally substituted with one or more halogens; each $R_3$ is independently hydrogen, cyano, or $(C_{1-10})$alkyl optionally substituted with one or more halogens; and each $R_4$ is independently hydrogen, cyano, or $(C_{1-10})$alkyl optionally substituted with one or more halogens.

Another encompasses compounds of formula IIA:

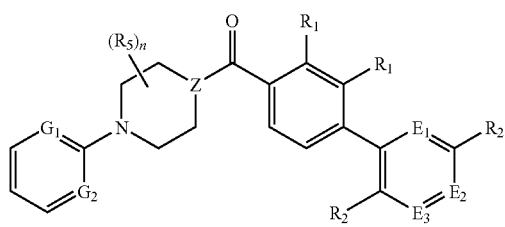

(IIA)

and pharmaceutically acceptable salts and solvates thereof, wherein: Z is $CR_5$ or N; each $R_5$ is independently halogen, cyano, $R_{5A}$, $OR_{5A}$, $C(O)R_{5A}$, $C(O)OR_{5A}$, $C(O)N(R_{5A}R_{5B})$, $N(R_{5A}R_{5B})$, or $SO_2R_{5A}$; each $R_{5A}$ is independently hydrogen or optionally substituted alkyl, aryl, arylalkyl, alkylaryl, heterocycle, heterocycle-alkyl, or alkyl-heterocycle; each $R_{5B}$ is independently hydrogen or optionally substituted alkyl, aryl, arylalkyl, alkylaryl, heterocycle, heterocycle-alkyl, or alkyl-heterocycle; and n is 0-5 if Z is $CR_5$, or 0-4 if Z is N.

Another encompasses compounds of formula IIB:

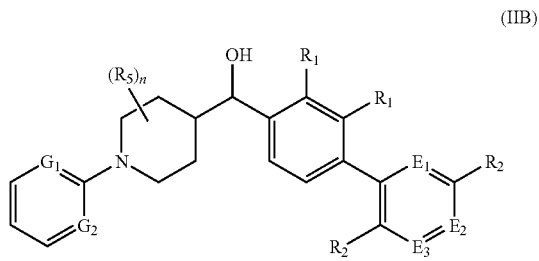

(IIB)

and pharmaceutically acceptable salts and solvates thereof.

Another encompasses compounds of formula IIC:

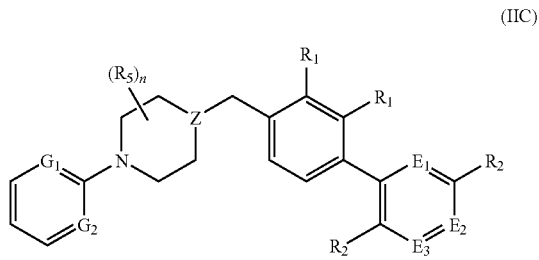

(IIC)

and pharmaceutically acceptable salts and solvates thereof, wherein: Z is $CR_5$ or N; each $R_5$ is independently halogen, cyano, $R_{5A}$, $OR_{5A}$, $C(O)R_{5A}$, $C(O)OR_{5A}$, $C(O)N(R_{5A}R_{5B})$, $N(R_{5A}R_{5B})$, or $SO_2R_{5A}$; each $R_{5A}$ is independently hydrogen or optionally substituted alkyl, aryl, arylalkyl, alkylaryl, heterocycle, heterocycle-alkyl, or alkyl-heterocycle; each $R_{5B}$ is independently hydrogen or optionally substituted alkyl, aryl, arylalkyl, alkylaryl, heterocycle, heterocycle-alkyl, or alkyl-heterocycle; and n is 0-5 if Z is $CR_5$, or 0-4 if Z is N.

In one embodiment of the invention encompassed by formula II (and IIA-C, as appropriate), at least one of $G_1$, $G_2$, $J_1$, $J_2$ or $J_3$ is N. In another, at least one of $J_1$, $J_2$ and $J_3$ is $CR_4$. In another, if Y is C(O), A is piperazine, all of $G_1$, $G_2$, $J_1$, $J_3$, $D_1$, $D_2$, $E_1$, and $E_3$ are CH, and all of $R_1$ are hydrogen, then none of $R_2$ are lower alkyl. In another, if Y is C(O), A is piperazine, $D_2$ and $E_1$ are both N, and all of $R_1$ and $R_2$ are hydrogen, then $R_4$ is not cyano. In another, if Y is O, A is pyrrolidine, all of $G_1$, $G_2$, $J_1$, $J_3$, $D_1$, $D_2$, $E_1$, $E_2$, and $E_3$ are CH, and all of $R_1$ are hydrogen, then at least one $R_2$ is not hydrogen. In another, if Y is $CH_2$, A is piperazine, all of $G_2$, $J_1$, $J_2$, $J_3$, $D_1$, and $D_2$ are CH, all of $E_1$, $E_2$ and $E_3$ are $CR_2$, and all of $R_1$ are hydrogen, at least one $R_2$ is not hydrogen. In another, if Y is C(O) or $CH_2$, A is piperazine, at least one of $G_1$ and $G_2$ is N, all of $J_1$, $J_2$, $J_3$, $D_1$, $D_2$, $E_1$, $E_2$ and $E_3$ are CH, and all of $R_1$ are hydrogen, then at least one $R_2$ is not hydrogen.

Various other embodiments of the invention, which pertain to each of the above formulae (e.g., I, IA-F, II and IIA-C) when appropriate (when the particular formula contains the moiety referred to), are as follows.

In one, A is optionally substituted non-aromatic heterocycle containing no more than two nitrogen atoms (i.e., the heterocycle, which contains no more than two nitrogen atoms, is optionally substituted).

In another, A is monocyclic. In another, A is bicyclic. In another, A is unsubstituted. In another, A is optionally substituted pyrrolidine, piperidine, piperazine, hexahydropyrimidine, 1,2,3,6-tetrahydropyridine, octahydrocyclopenta[c]pyrrole, or octahydropyrrolo[3,4-c]pyrrole.

In another, one of $D_1$ and $D_2$ is N. In another, both $D_1$ and $D_2$ are N. In another, both $D_1$ and $D_2$ are $CR_1$.

In another, one of $E_1$, $E_2$ and $E_3$ is N. In another, two of $E_1$, $E_2$ and $E_3$ are N. In another, all of $E_1$, $E_2$ and $E_3$ are N. In another, all of $E_1$, $E_2$ and $E_3$ are independently $CR_2$.

In another, $R_1$ is hydrogen, halogen, or optionally substituted alkyl. In another, $R_1$ is $OR_4$ and, for example, $R_4$ is hydrogen or optionally substituted alkyl.

In another, $R_2$ is hydrogen, halogen, or optionally substituted alkyl. In another, $R_2$ is $OR_4$ and, for example, $R_4$ is hydrogen or optionally substituted alkyl.

In another, X is an optionally substituted 5-, 6-, 9- or 10-membered heteroaryl. In another, X is optionally substituted 5- or 6-membered heteroaryl. In another, X is of the formula:

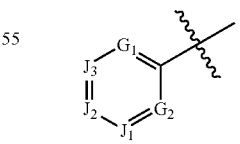

wherein: each of $G_1$ and $G_2$ are independently N or $CR_3$; each of $J_1$, $J_2$ and $J_3$ are independently N or $CR_4$; each $R_3$ is independently hydrogen, halogen, cyano, $R_A$, $OR_A$, $C(O)R_A$, $C(O)OR_A$, $C(O)N(R_AR_B)$, $N(R_AR_B)$, or $SO_2R_A$; and each $R_4$ is independently hydrogen, halogen, cyano, $R_A$, $OR_A$, $C(O)R_A$, $C(O)OR_A$, $C(O)N(R_AR_B)$, $N(R_AR_B)$, or $SO_2R_A$; provided that at least one of $J_1$, $J_2$ and $J_3$ is $CR_4$.

In another, one of G$_1$ and G$_2$ is N. In another, both G$_1$ and G$_2$ are N. In another, both G$_1$ and G$_2$ are CR$_3$.

In another, one of J$_1$, J$_2$ and J$_3$ is N. In another, two of J$_1$, J$_2$ and J$_3$ are N. In another, all of J$_1$, J$_2$ and J$_3$ are independently CR$_4$.

In another, R$_3$ is hydrogen, halogen, or optionally substituted alkyl. In another, R$_3$ is OR$_A$ and, for example, R$_A$ is hydrogen or optionally substituted alkyl.

In another, R$_4$ is hydrogen, halogen, or optionally substituted alkyl. In another, R$_4$ is OR$_A$ and, for example, R$_A$ is hydrogen or optionally substituted alkyl.

In another, Y is C(O). In another, Y is CH(OH). In another, Y is CH$_2$.

Examples of specific compounds include:
(1-(pyrimidin-2-yl)piperidin-4-yl)(4'-(trifluoromethyl)biphenyl-4-yl)methanol;
(4'-chlorobiphenyl-4-yl)(2,6-dimethyl-4-(pyridin-2-yl)piperazin-1-yl)methanone;
(3'-chloro-3-methoxybiphenyl-4-yl)(1-(pyrimidin-2-yl)piperidin-4-yl)methanone;
(4-(pyrimidin-2-yl)piperazin-1-yl)(4'-(trifluoromethyl)biphenyl-4-yl)methanone;
(3-fluoro-4'-methylbiphenyl-4-yl)(4-(pyrimidin-2-yl)piperazin-1-yl)methanone;
(4'-chlorobiphenyl-4-yl)(4-(pyrimidin-2-yl)piperazin-1-yl)methanone;
(2'-methylbiphenyl-4-yl)(4-(pyrimidin-2-yl)piperazin-1-yl)methanone;
(4-(benzo[d]oxazol-2-yl)piperazin-1-yl)(4'-(trifluoromethyl)biphenyl-4-yl)methanone;
biphenyl-4-yl(4-(4-(trifluoromethyl)pyrimidin-2-yl)piperazin-1-yl)methanone;
(S)-(2-benzyl-4-(pyrimidin-2-yl)piperazin-1-yl)(4'-(trifluoromethyl)biphenyl-4-yl)methanone;
(5-(pyrimidin-2-yl)hexahydropyrrolo[3,4-c]pyrrol-2(1H)-yl)(6-p-tolylpyridin-3-yl)methanone;
(5-(pyrimidin-2-yl)hexahydropyrrolo[3,4-c]pyrrol-2(1H)-yl)(6-(3-(trifluoromethyl)phenyl)pyridin-3-yl)methanone;
(6-(4-chlorophenyl)pyridin-3-yl)(5-(pyrimidin-2-yl)hexahydropyrrolo[3,4-c]pyrrol-2(1H)-yl)methanone;
(5-(pyrimidin-2-yl)hexahydropyrrolo[3,4-c]pyrrol-2(1H)-yl)(6-(4-(trifluoromethyl)phenyl)pyridin-3-yl)methanone;
(5-(4-chlorophenyl)isoxazol-3-yl)(4-(pyrimidin-2-yl)piperazin-1-yl)methanone;
(3'-chlorobiphenyl-4-yl)(1-(pyridin-2-yl)piperidin-4-yl)methanone;
biphenyl-4-yl(4-(pyrimidin-2-yl)-1,4-diazepan-1-yl)methanone;
(8-(pyrimidin-2-yl)-8-azabicyclo[3.2.1]octan-3-yl)(4'-(trifluoromethyl)biphenyl-4-yl)methanone;
biphenyl-4-yl(1-(pyrimidin-2-yl)azetidin-3-yl)methanone;
(6-(4-chloro-3-(trifluoromethyl)phenyl)pyridin-3-yl)(4-(pyrimidin-2-yl)piperazin-1-yl)methanone;
(6-(4-chloro-3-methylphenyl)pyridin-3-yl)(4-(pyrimidin-2-yl)piperazin-1-yl)methanone;
(4'-chlorobiphenyl-4-yl)(1-(pyridin-2-yl)piperidin-4-yl)methanone;
(2-methylbiphenyl-4-yl)(4-(pyrimidin-2-yl)piperazin-1-yl)methanone;
(3,4'-dimethylbiphenyl-4-yl)(4-(pyrimidin-2-yl)piperazin-1-yl)methanone;
(5-(3-chlorophenyl)pyridin-2-yl)(4-(pyrimidin-2-yl)piperazin-1-yl)methanone;
(4-(pyrimidin-2-yl)piperazin-1-yl)(5-p-tolylpyridin-2-yl)methanone;
(4-(pyridin-2-yl)piperazin-1-yl)(3'-(trifluoromethyl)biphenyl-4-yl)methanone;
(1-(pyrimidin-2-yl)piperidin-4-yl)(4'-(trifluoromethyl)biphenyl-4-yl)methanone;
(3-fluoro-3'-(trifluoromethyl)biphenyl-4-yl)(4-(pyrimidin-2-yl)piperazin-1-yl)methanone;
(4-(pyrimidin-2-yl)piperazin-1-yl)(3'-(trifluoromethoxy)biphenyl-4-yl)methanone;
(5-(pyrimidin-2-yl)hexahydropyrrolo[3,4-c]pyrrol-2(1H)-yl)(3'-(trifluoromethyl)biphenyl-4-yl)methanone;
biphenyl-4-yl(5-(pyrimidin-2-yl)hexahydropyrrolo[3,4-c]pyrrol-2(1H)-yl)methanone;
(1-phenyl-5-(pyrimidin-2-yl)hexahydropyrrolo[3,4-c]pyrrol-2(1H)-yl)(4'-(trifluoromethyl)biphenyl-4-yl)methanone;
biphenyl-4-yl(4-(thiazol-2-yl)piperazin-1-yl)methanone;
(4-(4-chlorophenyl)cyclohexyl)(4-(pyrimidin-2-yl)piperazin-1-yl)methanone;
4'-(4-(pyrimidin-2-yl)piperazine-1-carbonyl)biphenyl-3-carbonitrile;
(4'-(methylsulfonyl)biphenyl-4-yl)(4-(pyrimidin-2-yl)piperazin-1-yl)methanone;
2-(4-((3'-chlorobiphenyl-4-yl)(hydroxy)methyl)piperidin-1-yl)pyrimidin-5-ol;
(4-(pyridin-3-yl)phenyl)(4-(pyrimidin-2-yl)piperazin-1-yl)methanone;
(3'-chloro-3-hydroxybiphenyl-4-yl)(1-(pyrimidin-2-yl)piperidin-4-yl)methanone;
1-(4'-(4-(pyrimidin-2-yl)piperazine-1-carbonyl)biphenyl-3-yl)ethanone;
(2',4'-difluoro-3-methylbiphenyl-4-yl)(4-(pyrimidin-2-yl)piperazin-1-yl)methanone;
(5-phenyl-1H-pyrrol-2-yl)(4-(pyrimidin-2-yl)piperazin-1-yl)methanone;
(6-(4-chlorophenyl)pyridin-3-yl)(4-(pyrimidin-2-yl)piperazin-1-yl)methanone;
(5'-chloro-2'-fluorobiphenyl-4-yl)(8-(pyrimidin-2-yl)-8-azabicyclo[3.2.1]octan-3-yl)methanone;
2-(4-(biphenylcarbonyl)piperazin-1-yl)nicotinonitrile;
2-(4-(biphenyl-4-yloxy)piperidin-1-yl)pyrimidine;
(2'-fluoro-5'-(trifluoromethyl)biphenyl-4-yl)(1-(pyrimidin-2-yl)pyrrolidin-3-yl)methanone;
(4-(4-methylthiophen-2-yl)phenyl)(1-(pyrimidin-2-yl)piperidin-4-yl)methanone;
(4'-fluorobiphenyl-4-yl)(4-(pyrimidin-2-yl)piperazin-1-yl)methanone;
(2-fluoro-4'-methylbiphenyl-4-yl)(4-(pyrimidin-2-yl)piperazin-1-yl)methanone;
biphenyl-4-yl(3-methyl-4-(pyrimidin-2-yl)piperazin-1-yl)methanone;
(2'-fluoro-5'-(trifluoromethyl)biphenyl-4-yl)(4-methyl-1-(pyrimidin-2-yl)piperidin-4-yl)methanone;
biphenyl-4-yl(4-(5-methylpyridin-2-yl)piperazin-1-yl)methanone;
biphenyl-4-yl(2-methyl-4-(pyrimidin-2-yl)piperazin-1-yl)methanone;
(1-(pyridin-2-yl)piperidin-4-yl)(3'-(trifluoromethyl)biphenyl-4-yl)methanone;
(6-(3-chlorophenyl)pyridin-3-yl)(4-(pyrimidin-2-yl)piperazin-1-yl)methanone;
(4-(pyrimidin-2-yl)piperazin-1-yl)(6-(3-(trifluoromethyl)phenyl)pyridin-3-yl)methanone;
(4-(pyrimidin-2-yl)piperazin-1-yl)(6-p-tolylpyridin-3-yl)methanone;
(4'-chloro-3'-(trifluoromethyl)biphenyl-4-yl)(1-(pyrimidin-2-yl)piperidin-4-yl)methanone;

(4-(2-chloropyridin-4-yl)phenyl)(4-(pyrimidin-2-yl)piperazin-1-yl)methanone;
(2',4'-difluorobiphenyl-4-yl)(4-(pyrimidin-2-yl)piperazin-1-yl)methanone;
(6-(2,4-difluorophenyl)pyridin-3-yl)(4-(pyrimidin-2-yl)piperazin-1-yl)methanone;
(3',5'-dichlorobiphenyl-4-yl)(4-(pyrimidin-2-yl)piperazin-1-yl)methanone;
2-(4-(biphenyl-4-ylmethyl)piperazin-1-yl)pyrimidine;
(4'-chlorobiphenyl-4-yl)(1-(pyrimidin-2-yl)piperidin-4-yl)methanone;
(6-(3-chlorophenyl)pyridin-3-yl)(5-(pyrimidin-2-yl)hexahydropyrrolo[3,4-c]pyrrol-2(1H)-yl)methanone;
(1-(pyridin-2-yl)piperidin-4-yl)(4'-(trifluoromethyl)biphenyl-4-yl)methanone;
(2'-fluoro-5'-(trifluoromethyl)biphenyl-4-yl)(4-(pyrimidin-2-yl)piperazin-1-yl)methanone;
(4'-methylbiphenyl-4-yl)(4-(pyrimidin-2-yl)piperazin-1-yl)methanone;
biphenyl-4-yl(4-(5-methylpyridin-2-yl)piperazin-1-yl)methanone;
1-(biphenylcarbonyl)-4-(pyrimidin-2-yl)piperazin-2-one;
biphenyl-4-yl(1-(pyrimidin-2-yl)-1,2,3,6-tetrahydropyridin-4-yl)methanone;
(3'-chlorobiphenyl-4-yl)(1-(pyrimidin-2-yl)piperidin-4-yl)methanone;
biphenyl-4-yl(1-(pyrimidin-2-yl)-1,2,3,6-tetrahydropyridin-4-yl)methanol;
(3'-chlorobiphenyl-4-yl)(4-(pyrimidin-2-yl)piperazin-1-yl)methanone;
(4-(pyrimidin-2-yl)piperazin-1-yl)(3'-(trifluoromethyl)biphenyl-4-yl)methanone;
(3'-chlorobiphenyl-4-yl)(1-(5-hydroxypyrimidin-2-yl)piperidin-4-yl)methanone;
(4'-ethylbiphenyl-4-yl)(4-(pyrimidin-2-yl)piperazin-1-yl)methanone;
biphenyl-4-yl(4-(4-methylpyrimidin-2-yl)piperazin-1-yl)methanone;
(6-(2,4-difluorophenyl)pyridin-3-yl)(5-(pyrimidin-2-yl)hexahydropyrrolo[3,4-c]pyrrol-2(1H)-yl)methanone;
(4'-chlorobiphenyl-4-yl)(4-(pyridin-2-yl)piperazin-1-yl)methanone;
(5-methyl-1-(pyrimidin-2-yl)-1,2,3,6-tetrahydropyridin-4-yl)(4'-(trifluoromethyl)biphenyl-4-yl)methanone;
biphenyl-4-yl(4-(5-ethylpyrimidin-2-yl)piperazin-1-yl)methanone;
(4-(pyridin-2-yl)piperazin-1-yl)(4'-(trifluoromethyl)biphenyl-4-yl)methanone;
(4-(pyridin-2-yl)phenyl)(4-(pyrimidin-2-yl)piperazin-1-yl)methanone;
biphenyl-4-yl(4-(pyrazin-2-yl)piperazin-1-yl)methanone;
(4'-methoxybiphenyl-4-yl)(4-(pyrimidin-2-yl)piperazin-1-yl)methanone;
biphenyl-4-yl(4-(6-methylpyridazin-3-yl)piperazin-1-yl)methanone;
4'-(4-(pyrimidin-2-yl)piperazine-1-carbonyl)biphenyl-4-carbonitrile;
(2,6-dimethyl-4-(pyridin-2-yl)piperazin-1-yl)(4'-(trifluoromethyl)biphenyl-4-yl)methanone;
(5-phenylthiophen-2-yl)(4-(pyrimidin-2-yl)piperazin-1-yl)methanone;
(6-(5-methylthiophen-2-yl)pyridin-3-yl)(4-(pyrimidin-2-yl)piperazin-1-yl)methanone;
biphenyl-4-yl(4-(pyridin-4-yl)piperazin-1-yl)methanone;
(R)-(2-methyl-4-(pyrimidin-2-yl)piperazin-1-yl)(4'-(trifluoromethyl)biphenyl-4-yl)methanone;
biphenyl-4-yl((2S,5S)-2,5-dimethyl-4-(pyrimidin-2-yl)piperazin-1-yl)methanone;
(3'-chlorobiphenyl-4-yl)(4-(pyridin-2-yl)piperazin-1-yl)methanone;
(4-(pyrimidin-2-yl)piperazin-1-yl)(2'-(trifluoromethyl)biphenyl-4-yl)methanone;
(S)-(4'-chlorobiphenyl-4-yl)(2-methyl-4-(pyrimidin-2-yl)piperazin-1-yl)methanone;
(5'-chloro-2'-fluorobiphenyl-4-yl)(4-(pyrimidin-2-yl)piperazin-1-yl)methanone;
(4-(5-methylthiophen-2-yl)phenyl)(1-(pyrimidin-2-yl)piperidin-4-yl)methanone;
biphenyl-4-yl(4-(4,6-dimethylpyrimidin-2-yl)piperazin-1-yl)methanone;
(S)-(2-methyl-4-(pyrimidin-2-yl)piperazin-1-yl)(4'-(trifluoromethyl)biphenyl-4-yl)methanone;
(S)-(2-benzyl-4-(pyrimidin-2-yl)piperazin-1-yl)(4'-chlorobiphenyl-4-yl)methanone;
biphenyl-4-yl(4-(pyridazin-3-yl)piperazin-1-yl)methanone;
(6-(4-methylthiophen-2-yl)pyridin-3-yl)(4-(pyrimidin-2-yl)piperazin-1-yl)methanone;
1-(2',4'-difluorobiphenylcarbonyl)-4-(pyrimidin-2-yl)piperazine-2-carbonitrile;
(4'-chlorobiphenyl-4-yl)((2S,5S)-2,5-dimethyl-4-(pyrimidin-2-yl)piperazin-1-yl)methanone;
biphenyl-4-yl(2-tert-butyl-4-(pyrimidin-2-yl)piperazin-1-yl)methanone;
(S)-biphenyl-4-yl(2-isopropyl-4-(pyrimidin-2-yl)piperazin-1-yl)methanone;
biphenyl-4-yl(2,6-dimethyl-4-(pyrimidin-2-yl)piperazin-1-yl)methanone;
(3'-chloro-2'-fluorobiphenyl-4-yl)(4-(pyrimidin-2-yl)piperazin-1-yl)methanone;
(4-(pyrimidin-2-yl)piperazin-1-yl)(6-(4-(trifluoromethyl)phenyl)pyridin-3-yl)methanone;
(4'-chloro-3'-methylbiphenyl-4-yl)(1-(pyrimidin-2-yl)piperidin-4-yl)methanone;
(3'-chloro-2-fluorobiphenyl-4-yl)(4-(pyrimidin-2-yl)piperazin-1-yl)methanone;
(2,6-dimethyl-4-(pyridin-2-yl)piperazin-1-yl)(4'-methylbiphenyl-4-yl)methanone;
3'-chloro-4-(1-(pyrimidin-2-yl)piperidine-4-carbonyl)biphenyl-3-yl acetate;
biphenyl-4-yl(2-methyl-4-(pyridin-2-yl)piperazin-1-yl)methanone;
1-(biphenyl-4-ylmethyl)-4-(pyrimidin-2-yl)piperazin-2-one;
(3',4'-dichlorobiphenyl-4-yl)(4-(pyrimidin-2-yl)piperazin-1-yl)methanone;
(3'-chlorobiphenyl-4-yl)(8-(pyrimidin-2-yl)-8-azabicyclo[3.2.1]octan-3-yl)methanol;
(S)-biphenyl-4-yl(2-isobutyl-4-(pyrimidin-2-yl)piperazin-1-yl)methanone;
(3'-chlorobiphenyl-4-yl)(8-(pyrimidin-2-yl)-8-azabicyclo[3.2.1]octan-3-yl)methanone;
(S)-(4'-chlorobiphenyl-4-yl)(2-isopropyl-4-(pyrimidin-2-yl)piperazin-1-yl)methanone;
(4'-methylbiphenyl-4-yl)(4-(pyridin-2-yl)piperazin-1-yl)methanone;
(S)-(2-isopropyl-4-(pyrimidin-2-yl)piperazin-1-yl)(4'-(trifluoromethyl)biphenyl-4-yl)methanone;
(3'-chlorobiphenyl-4-yl)(1-(pyrimidin-2-yl)piperidin-4-yl)methanol;
(S)-(2-isobutyl-4-(pyrimidin-2-yl)piperazin-1-yl)(4'-(trifluoromethyl)biphenyl-4-yl)methanone;
(S)-(4'-chlorobiphenyl-4-yl)(2-isobutyl-4-(pyrimidin-2-yl)piperazin-1-yl)methanone;

(3'-chlorobiphenyl-4-yl)(1-(pyrimidin-2-yl)pyrrolidin-3-yl)methanone;
(2',4'-difluorobiphenyl-4-yl)(8-(pyrimidin-2-yl)-8-azabicyclo[3.2.1]octan-3-yl)methanone;
4'-(4-(pyridin-2-yl)piperazine-1-carbonyl)biphenyl-4-carbonitrile;
(4-(pyrimidin-2-yl)-1,4-diazepan-1-yl)(3'-(trifluoromethyl)biphenyl-4-yl)methanone;
methyl 1-(5'-chloro-2'-fluorobiphenylcarbonyl)-4-(pyrimidin-2-yl)piperazine-2-carboxylate;
(4-(benzo[d]oxazol-2-yl)piperazin-1-yl)(4'-chlorobiphenyl-4-yl)methanone;
(3'-chlorobiphenyl-4-yl)(4-(thiazol-2-yl)piperazin-1-yl)methanone;
(4-(5-chlorothiophen-2-yl)phenyl)(1-(pyrimidin-2-yl)piperidin-4-yl)methanone;
1-(5'-chloro-2'-fluorobiphenylcarbonyl)-4-(pyrimidin-2-yl)piperazine-2-carbonitrile;
(4-phenylthiophen-2-yl)(4-(pyrimidin-2-yl)piperazin-1-yl)methanone;
biphenyl-4-yl(4-(pyrimidin-2-yl)-3,4-dihydroquinoxalin-1(2H)-yl)methanone;
(5'-chloro-2'-fluorobiphenyl-4-yl)(8-(pyrimidin-2-yl)-8-azabicyclo[3.2.1]octan-3-yl)methanol;
(5-phenylfuran-2-yl)(4-(pyrimidin-2-yl)piperazin-1-yl)methanone;
(4'-chlorobiphenyl-4-yl)(5-(pyrimidin-2-yl)hexahydropyrrolo[3,4-c]pyrrol-2(1H)-yl)methanone;
4-(4'-chlorobiphenyl-4-yl)-1-(pyrimidin-2-yl)piperidin-4-ol;
(5-(pyrimidin-2-yl)hexahydropyrrolo[3,4-c]pyrrol-2(1H)-yl)(4'-(trifluoromethyl)biphenyl-4-yl)methanone;
biphenyl-4-yl(5-(pyridin-2-yl)hexahydropyrrolo[3,4-c]pyrrol-2(1H)-yl)methanone;
(3'-chlorobiphenyl-4-yl)(5-(pyrimidin-2-yl)hexahydropyrrolo[3,4-c]pyrrol-2(1H)-yl)methanone;
biphenyl-4-yl((2S,5S)-2,5-dimethyl-4-(pyrimidin-2-yl)piperazin-1-yl)methanone;
1-((3'-chlorobiphenyl-4-yl)methyl)-N,N-dimethyl-4-(pyrimidin-2-yl)piperazine-2-carboxamide;
(2',4'-difluorobiphenyl-4-yl)(3-methyl-1-(pyrimidin-2-yl)piperidin-4-yl)methanone;
(4-(benzo[d]thiazol-2-yl)piperazin-1-yl)(biphenyl-4-yl)methanone;
biphenyl-4-yl(4-(quinolin-2-yl)piperazin-1-yl)methanone;
4-(biphenyl-4-yl)-1-(pyrimidin-2-yl)piperidin-4-ol;
4'-chloro-N-methyl-N-(2-(methyl(pyrimidin-2-yl)amino)ethyl)biphenyl-4-carboxamide; and
2-(biphenyl-4-yl)-1-(4-(pyrimidin-2-yl)piperazin-1-yl)ethanone.

Preferred compounds of the invention are specific proline transporter inhibitors. Particular specific proline transporter inhibitors have a PTIC$_{50}$ of less than about 150, 125, 100, 75, 50 or 25 nM.

Some compounds inhibit the murine Na$^+$-dependent proline transporter, as determined by the method described in the Examples below, with an IC$_{50}$ of less than about 150, 125, 100, 75, 50 or 25 nM.

Some compounds do not significantly inhibit the dopamine transporter. For example, some specific proline transporter inhibitors inhibit the dopamine transporter with an IC$_{50}$ of greater than about 0.5, 1, 2.5, 5, or 10 µM as determined using the assay described in the Examples below.

Some compounds do not significantly inhibit the glycine transporter. For example, some specific proline transporter inhibitors inhibit the glycine transporter with an IC$_{50}$ of greater than about 0.5, 1, 2.5, 5, or 10 µM as determined using the assay described in the Examples below.

5.3. Preparation of Compounds

Compounds of the invention may be obtained or prepared using synthetic methods known in the art, as well as those described herein. For example, various piperazine-based compounds can be prepared according to the general approach shown in Scheme I:

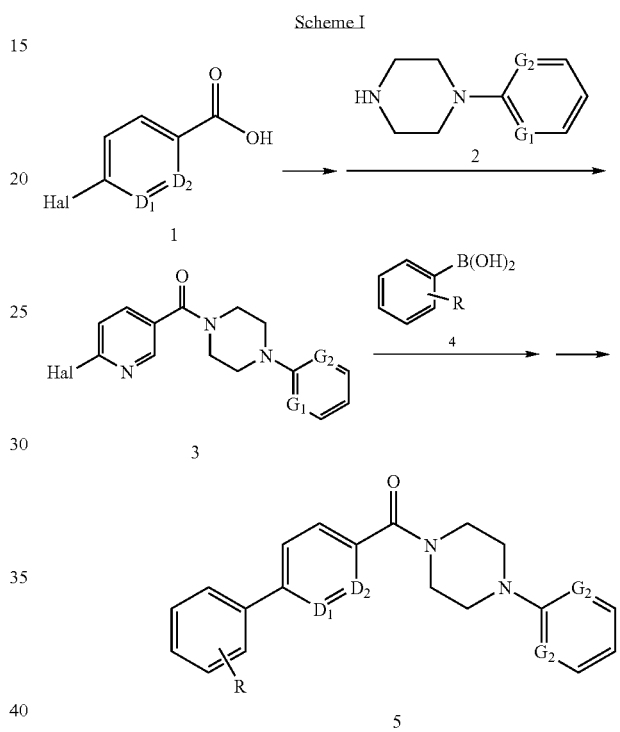

In this approach, a compound of formula 1 (D$_1$ and D$_2$ are defined herein) is contacted with a compound of formula 2 (G$_1$ and G$_2$ are defined herein) under suitable conditions to provide a compound of formula 3. Suitable conditions include, for example, EDCl, HOBt, and Hunig's base in DMF. Compound 3 is then contacted with compound 4 under suitable conditions to provide a compound of formula 5. Suitable conditions include, for example, Pd(Ph$_3$P)$_4$, K$_3$PO$_4$, DME, water and heat.

Various piperidine-based compounds can be prepared according to the general approach shown below in Scheme II:

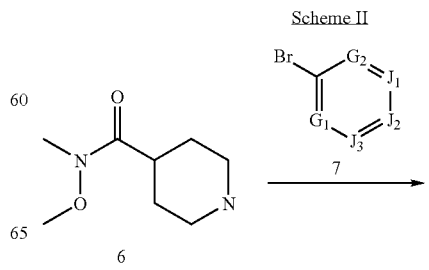

-continued

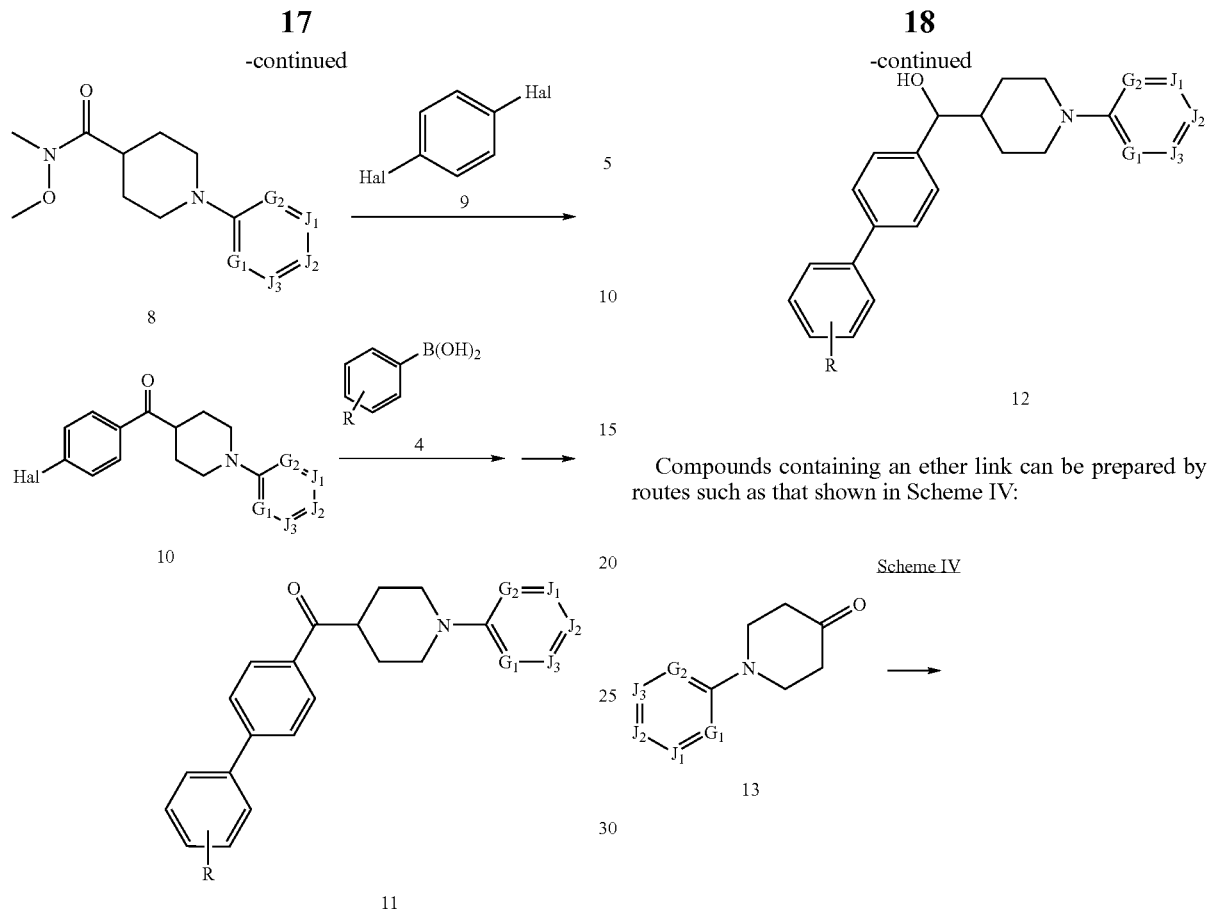

In this approach, a compound of formula 6 (e.g., as a TFA salt) is contacted with a compound of formula 7 ($G_1$, $G_2$, $J_1$, $J_2$ and $J_3$ are defined herein) under suitable conditions to provide compound 8. Suitable conditions include, for example, TEA and heat. Compound 8 is then contacted with compound 9 under suitable conditions to provide compound 10. Here, suitable conditions include, for example, n-BuLi in THF. Compound 10 is then contacted with a compound of formula 4 to provide the final compound, 11. Here, suitable conditions include, for example, Pd(Ph$_3$P)$_4$, K$_3$PO$_4$, DME, water and heat.

If desired, compounds of formula 11 can be reduced under suitable conditions (e.g., sodium borohydride) to provide compounds of formula 12, as shown below in Scheme III:

Compounds containing an ether link can be prepared by routes such as that shown in Scheme IV:

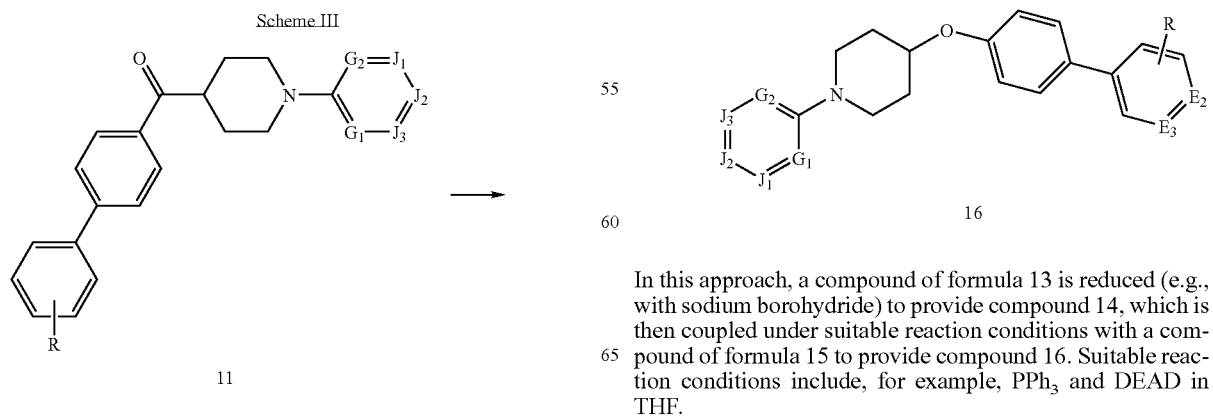

In this approach, a compound of formula 13 is reduced (e.g., with sodium borohydride) to provide compound 14, which is then coupled under suitable reaction conditions with a compound of formula 15 to provide compound 16. Suitable reaction conditions include, for example, PPh$_3$ and DEAD in THF.

Compounds containing a methylene link can be prepared by routes such as that shown in Scheme V:

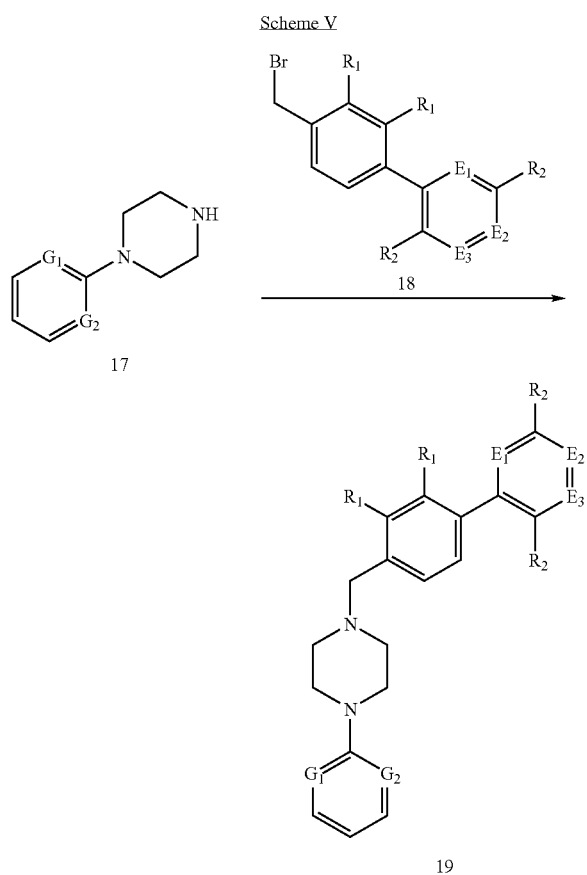

In this approach, a compound of formula 17 is contacted with compound 18 under suitable reaction conditions to provide compound 19. Suitable reaction conditions include, for example, potassium carbonate in DMF.

Some specific reaction conditions that can be used in the various synthetic schemes shown above are provided in the Examples, below.

5.4. Methods of Treatment

One embodiment of this invention encompasses a method of inhibiting a proline transporter, which comprises contacting a proline transporter (in vitro or in vivo) with a sufficient amount of a compound of the invention. Preferred proline transporters are encoded by the human gene SLC6A7, the murine ortholog thereof, or a nucleic acid molecule that encodes a proline transporter and that hybridizes under standard conditions to the full length of either.

Another embodiment encompasses a method of improving the cognitive performance of a human patient, which comprises administering to the patient an effective amount of a compound of the invention. Examples of improved cognitive performance include enhanced learning (e.g., learning more quickly), improved comprehension, improved reasoning, and improved short- and/or long-term memory.

Another embodiment encompasses a method of treating, managing or preventing a disease or disorder in a human patient, which comprises administering to the patient a therapeutically or prophylactically effective amount of a compound of the invention. Examples of diseases and disorders include Alzheimer's disease, autism, cognitive disorders (e.g., difficulty in thinking, reasoning, or problem solving), dementia, learning disorders (e.g., dyslexia, dyscalculia, dysgraphia, dysphasia, dysnomia), and short- and long-term memory loss. Additional disorders include adverse sequelae of brain damage caused by, for example, oxygen starvation, traumatic injury or stroke.

5.5. Pharmaceutical Compositions

This invention encompasses pharmaceutical compositions and dosage forms comprising compounds of the invention as their active ingredients. Pharmaceutical compositions and dosage forms of this invention may optionally contain one or more pharmaceutically acceptable carriers or excipients. Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration may require enteric coatings to protect the active ingredient from degradation within the gastrointestinal tract. In another example, the active ingredient may be administered in a liposomal formulation to shield it from degradative enzymes, facilitate transport in circulatory system, and/or effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

6. EXAMPLES

6.1. SLC6A7-Deficient Mice

To determine the effect of inhibiting the $Na^+$-dependent proline transporter, mice homozygous for a genetically engineered mutation in the murine ortholog of the human SLC6A7 gene ("knockout" or "KO" mice) were generated using correspondingly mutated ES cell clones from the OMNIBANK collection of mutated murine ES cell clones (see generally U.S. Pat. No. 6,080,576).

Mice that were heterozygous, homozygous, or wildtype for the mutated allele were produced by breeding heterozygous animals capable of germline transmission of the mutant allele. The mutated allele assorted according to standard Mendelian genetics. The mice were subjected to a battery of medical and behavioral tests, including those described below.

6.1.1. Trace Conditioning

Trace aversive conditioning measures a form of classical conditioning with temporal separation between the end of a conditioned stimulus (CS) (in this case an 80 db tone) and the onset of an unconditioned stimulus (US) (in this case a 0.7 mA electric current) that are separated by a temporal "trace" (approximately 30 seconds). This assay measures higher-order learning (usually associated with hippocampal function or the cortex) by determining how rapidly the test subjects learn to associate the US with CS. The test animals are scored by calculating the percent freezing time as determined by comparing the difference between percent freezing post-CS and the percent freezing pre-CS.

As shown in FIG. 1, both male and female animals that were homozygous for the mutation in the murine ortholog of the SLC6A7 gene displayed significantly higher freezing percentages (approximately 50 percent for an average of 16 test animals) as compared to their wildtype control counterparts (approximately 30 percent for an average of 16 control animals). These results indicate that homozygous mutant animals perform significantly better in this well established test for cognitive performance.

6.1.2. Water Maze

The Morris water maze used a circular pool 2 meters in diameter and 40 cm in depth. See, e.g., Morris, 1984, *J. Neurosci. Methods* 11:47-60, Guillou et al., 1999, *J. Neurosci.* 19:6183-90. The pool was filled to a depth of 30 cm with water at a temperature of 24-26° C., made opaque by the addition of non-toxic water-based paint. The "escape" platform was about 30 cm high with a plastic disc 18 cm in diameter on top. The platform was placed about 0.5 cm below the water surface. The mouse was released into the pool facing the wall from one of 4 start positions labeled as N (North), S (South), W (West) or E (East). A videotracking system comprising the camera and the WaterMaze image software (Actimetrics, Inc.) divided the pool into 4 equal quadrants designated as SE, SW, NE, and NW. The software calculates the latency to reach platform, distance to the platform, time spent in each quadrant, swimming speed, and other parameters.

Each trial lasted until the mouse climbed onto the platform or 90 seconds had elapsed. If the mouse did not reach the platform in 90 seconds, the experimenter took it out of the water and gently placed it on the platform. At the end of each trial the mouse remained on the platform for further 20 seconds. There were 4 trials with platform per day with 8-12 min inter-trial intervals. During the inter-trial interval the mouse was kept in a clean cage under a heat lamp.

Typically one of two basic protocols were used: the first includes visible and hidden platform phases, and the second only uses a hidden platform phase; both protocols end with a 2 day reversal phase.

The visible phase generally precedes the hidden platform phase. In the visible phase, the pool was surrounded with white curtains in order to hide all external-maze cues/references. During this phase, the platform was made visible with a metal cylinder 8 cm h×3 cm, which was put on the platform. The start position was the same on each trial, while platform location was randomly changed during the trials. This phase lasted for approximately 3 days.

In the hidden platform phase, the platform was no longer marked and the curtains were removed. A variety of extra-maze cues were optionally placed around the pool. Here the start position was changed every trial, while the platform remained in the same location. This phase typically lasted about 7 days.

Probe trials were run before the training trials on day 1 and 5 of the hidden phase, and on day 1 of the visible phase, and also after the last trial on day 3 of the visible phase. During the probe trial, the platform was removed from the pool and the mouse was placed in the pool facing the wall in the quadrant opposite from the platform quadrant. The mouse swam for 60 sec and the percentage of time spent in each quadrant was recorded.

In the reversal phase, on each of 2 days, 5 trials were run. During the first trial the platform location was the same as it was in the hidden phase. In the next four trials, the platform was moved to the opposite quadrant. On the following day the platform was there on first trial and then again moved to the left or right adjoining quadrant for the last 4 trials. The start position was always kept opposite to the platform location.

When the above methods were used with SLC6A7 KO mice (n=12) and WT (n=7) controls, mice were first subjected to the visible platform task. Repeated measures (RM) and analysis of variance (ANOVA) were used to analyze genotype effect on the latency to reach platform over 11 trials.

The trial effect was $F(10, 170)=8.57$, $p<0.001$; the Genotype effect: $F(1, 17)=0.65$, $p<0.43$, interaction Genotype× Trial: $F(10, 170)=0.42$, $p<0.93$. Initially, there was no difference between WT and KO subjects, but a significant decrease in the latency over trails was observed.

When the trials progressed to the hidden platform task, RM ANOVA revealed a significant effect of the trials on the latency to reach platform: $F(19, 323)=7.2$, $p<0.001$. There was also a significant effect of genotype on same parameter: $F(1, 17)=8.0$, $p<0.012$; interaction Genotype x Trials was $F(19, 323)=1.16$, $p<0.29$. Overall, KO subjects had significantly shorter latencies to platform. No significant difference in swimming speed was detected so faster swimming did not account for the faster performance by the KO animals.

During the reversal phase, RM ANOVA was run on 4 trials with the platform switched to another quadrant on each of two days. On both days of reversal phase effect of trials was significant: $Fs(3, 51)>6.4$, $p<0.001$ indicating that both genotypes relearn well. However, there was no significant difference between them on each day of reversal: $Fs(1, 17)<0.75$, $ps>0.39$, although KO mice did tend to reach the platform faster.

During probe trials, the percent of time spent in each quadrant was compared with 25% chance for WT and KO mice by non-parametric Mann-Whitney test. The first two probe trials run before hidden phase the percent time was not different from chance in each quadrant for both genotypes. In the third probe trial run on the fifth day of hidden phase, the platform quadrant time was significantly different from chance for WT [$p<0.05$] and KO mice [$p<0.001$]; and the opposite quadrant time was significantly different for KO mice [$p<0.001$].

The above data indicate that KO mice learned the hidden platform task more quickly than WT animals. The data further establish that the observed difference cannot be explained by differences in visual abilities or swimming speed between genotypes.

6.2. Preparation of (4-Pyrimidin-2-yl-piperazin-1-yl)-[4-(4-chloromethylphenylphenyl]-methanone

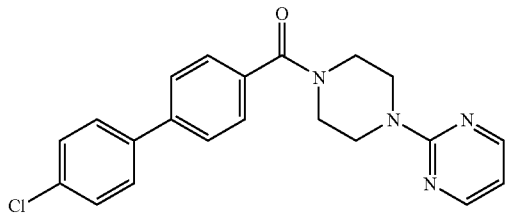 [SMILES: O=C(c1ccc(-c2ccc(Cl)cc2)cc1)N1CCN(c2ncccn2)CC1]

To a solution of 4-chloro-biphenyl-4-carboxylic acid (0.1 g, 0.43 mmol) and 1-(2-pyrimidyl)-piperazine (0.07 g, 0.43 mmol) in methylene chloride (3 ml), was added EDCl (0.098 g, 0.43 mmol) and HOAt (0.07 g, 0.43 mmol) triethylamine (0.07 ml, 0.52 mmol). The mixture was stirred for 16 hours and then washed with brine. The layers were separated, and the organic phase was dried over magnesium sulfate and concentrated. The resulting oil was purified by flash chromatography, and a white solid (0.11 g) was collected. Spectral data was consistent with structure. MS (M+1)=379. HPLC (>95%). $^1$H NMR (CDCl3) 8.35 (d, 2H), 7.55 (m, 8H), 6.58 (t, 1H), 3.80 (bm, 8H).

6.3. Preparation of (4-Pyrimidin-2-yl-piperazin-1-yl)[6-(3-trifluoromethyl-phenyl)-pyridin-3-yl]-methanone

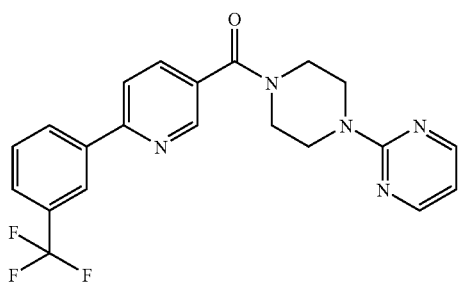 [SMILES: O=C(c1ccc(-c2cccc(C(F)(F)F)c2)nc1)N1CCN(c2ncccn2)CC1]

The title compound was prepared from (6-chloro-pyridin-3-yl)-(4-pyrimidin-2-yl-piperazin-1-yl)-methanone as described below.

(6-Chloro-pyridin-3-yl)-(4-pyrimidin-2-yl-piperazin-1-yl)-methanone

To a solution of chloronicotinic acid (2.51 g, 15.9 mmol) in DMF (64 ml), EDO (4.57 g, 23.9 mmol) and HOBt (3.23 g, 23.9 mmol) were added. Hunig's base (19.3 ml, 111 mmol) was added and the reaction was allowed to stir for 5 minutes. After this induction period, piperazine (4.52 g, 19.1 mmol) was added and the reaction stirred at room temperature. After stirring for 72 hours, the reaction was diluted with ethyl acetate and water. The layers were separated, and the aqueous portion was extracted twice more with ethyl acetate. The combined organic layers were washed with water three times and once with brine, dried over MgSO$_4$, filtered, and concentrated. The crude product was purified by silica gel chromatography using 20-25% acetone/hexanes, yielding the product (2.05 g, 42%) as a tan solid: $^1$H NMR (400 MHz, CDCl$_3$) δ 8.49 (d, J=1.8 Hz, 1H), 8.34 (d, J=4.7 Hz, 2H), 7.77 (dd, J=8.2, 2.4 Hz, 1H), 7.43 (d, J=8.1 Hz, 1H), 6.57 (t, J=4.8 Hz, 1H), 3.89 (bs, 6H), 3.52 (bs, 2H); m/z calcd. for C$_{14}$H$_{14}$ClN$_5$O: 303.08 found: (M+H)$^+$304.1; HPLC retention time=1.822 min (gradient of solvent B-0 to 100%; wavelength 254 nm), purity=100%.

(4-Pyrimidin-2-yl-piperazin-1-yl)-[6-(3-trifluoromethyl-phenyl)-pyridin-3-yl]-ethanone In a microwave reaction vessel, (6-chloro-pyridin-3-yl)-(4-pyrimidin-2-yl-piperazin-1-yl)-methanone (1.12 g, 3.69 mmol) was taken up in DME (15 ml). To this solution, boronic acid (1.36 g, 7.38 mmol), potassium phosphate (2.35 g, 11.1 mmol) and water (5 ml) were added. This mixture was then degassed using nitrogen, and the tetrakis triphenylphosphine palladium (0.426 g, 0.369 mmol) was added and the vessel sealed. The reaction was heated in the microwave at 160° C. for 5 minutes. After the reaction was complete, 1 N NaOH solution was added, and extraction twice with CH$_2$Cl$_2$ followed. The combined organic portions were washed with brine, dried, filtered, and concentrated. The crude product was purified by silica gel chromatography using 10-25% acetone in hexanes, yielding the final product (1.29 g, 85%) as a white solid: $^1$H NMR (400 MHz, CDCl$_3$) δ 8.80 (d, J=1.3 Hz, 1H), 8.34 (d, J=4.8 Hz, 2H), 8.32 (s, 1H), 8.22 (d, J=7.8 Hz, 1H), 7.93 (dd, J=8.1, 2.2 Hz, 1H), 7.87 (d, J=8.1 Hz, 1H), 7.72 (d, J=7.7 Hz, 1H), 7.63 (t, J=7.8 Hz, 1H), 6.57 (t, J=4.7 Hz, 1H), 3.91 (bs, 6H), 3.60 (bs, 2H); $^{13}$C NMR (100 MHz, CDCl$_3$) δ 167.81, 161.42, 157.80, 156.93, 148.18, 139.06, 136.46, 131.52, 131.20, 130.26, 130.17, 129.39, 126.20, 126.16, 126.13, 125.36, 123.99, 123.95, 123.92, 123.88, 122.65, 120.27, 110.69; m/z calcd. for C$_{21}$H$_{18}$F$_3$N$_5$O: 413.15 found: (M+H)$^+$414.05; HPLC retention time=3.233 min (gradient of solvent B-0 to 100%; wavelength 254 nm); purity=100%; mp=124-126° C.

6.4. Preparation of (4-Pyrimidin-2-yl-piperazin-1-yl)-(5-p-tolyl-pyridin-2-yl)-methanone

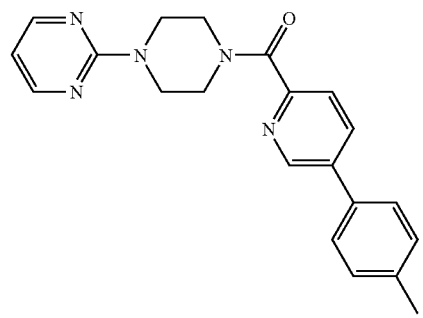 [SMILES: Cc1ccc(-c2ccc(C(=O)N3CCN(c4ncccn4)CC3)nc2)cc1]

To a solution of 5-bromo-2-iodopyridne (100 mg, 0.35 mmol, Song et al., Org. Lett., 6: 4905-4907 (2004)) in THF (1 ml) was added isopropyl magnesium chloride (2 M in THF, 0.185 ml) at 0° C. After being stirred for 45 minutes, a solution of 1-pyrimidin-2-yl-1,2,3,6-tetrahydro-pyridin-4-carboxylic acid methoxy-methyl amide (61 mg, 0.245 mmol) was added. The mixture was stirred at room temperature for another 1.5 hours and quenched with addition of water (15 ml) and EtOAc (50 ml). The aqueous phase was further extracted with EtOAc (20 ml). The combined organic layers were washed with brine (10 ml), dried (MgSO$_4$), filtered, and concentrated under reduced pressure to furnish the crude product. This material was purified by column chromatography (3% MeOH/CH$_2$Cl$_2$) to give (5-bromo-pyridin-2-yl)-(4- pyrimidin-2-yl-piperazin-1-yl)-methanone (25 mg, 25% for two steps) as a white solid: $^1$H NMR (CDCl$_3$, 400 MHz) δ 8.75 (m, 1H), 8.31 (d, J=6.4 Hz, 2H), 7.98 (m, 2H), 6.47 (t, J=6.4 Hz, 1H), 4.84 (m, 2H), 4.09 (m, 1H), 3.11 (m, 2H), 1.74 (m, 2H), 1.66 (m, 2H); MS calc'd. for $C_{14}H_{15}BrN_5O$ [M+H]$^+$: 349; Found: 349.

Following the general procedures for the Suzuki reactions, the title compound was obtained in 69% yield as an off-white solid: $^1$H NMR (CDCl$_3$, 400 MHz) δ 8.92 (m, 1H), 8.33 (d, J=6.4 Hz, 2H), 8.05 (m, 1H), 7.54 (m, 1H), 6.48 (t, J=6.4 Hz, 1H), 4.85 (m, 2H), 4.22 (m, 1H), 3.12 (m, 2H), 2.44 (s, 3H), 2.02 (m, 2H), 1.75 (m, 2H); MS calc'd. for $C_{21}H_{22}N_5O$ [M+H]$^+$: 359; Found: 359.

6.5. Preparation of (3.4.5.6-Tetrahydro-2H-[1,2'] bipyridinyl-4-yl)-(3'-trifluoromethyl-biphenyl-4-yl)-methanone

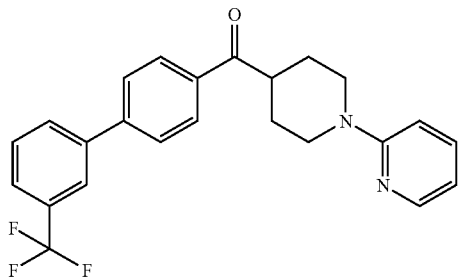 [SMILES: O=C(c1ccc(-c2cccc(C(F)(F)F)c2)cc1)C1CCN(c2ccccn2)CC1]

The title compound was prepared from (4-bromo-phenyl)-(3,4,5,6-tetrahydro-2H-[1,2+]bipyridinyl-4-yl)-methanone as described below.

3,4,5,6-Tetrahydro-2H-[1,2']bipyridinyl-4-carboxylic acid methoxy-methyl-amide

In a sealed tube, Weinreb amide (0.5515 g, 1.927 mmol) was taken up in absolute ethanol (10 ml) and 2-bromopyridine (0.19 ml, 1.927 mmol) and triethylamine (0.81 ml, 5.781 mmol) were added. The tube was sealed and heated at 150° C. for at least 48 hours. The reaction was then diluted with CH$_2$Cl$_2$, washed with water and brine, dried over MgSO$_4$, filtered, and concentrated. The crude product was purified by silica gel chromatography using 10-20% acetone in hexanes, yielding the product (0.1375 g, 29%) as a brown oil: $^1$H NMR (400 MHz, CDCl$_3$) δ 8.17 (dd, J=4.9, 1.2 Hz, 1H), 7.46 (m, 1H), 6.66 (d, J=8.6 Hz, 1H), 6.58 (m, 1H), 4.35 (dt, J=13.0, 2.9 Hz, 2H), 3.74 (s, 3H), 3.20 (s, 3H), 2.91 (m, 3H), 1.83 (m, 4H); m/z calcd. for $C_{13}H_{19}N_3O_2$: 249.15 found: (M+H)$^+$ 250.05; HPLC retention time=1.533 min (wavelength 220 nm), purity=98.4%.

(4-Bromo-phenyl)-(3,4,5,6-tetrahydro-2H-[1,2']bipyridinyl-4-yl)-methanone

A solution of 1,4-dibromobenzene (0.223 g, 0.944 mmol) in anhydrous THF (3.0 ml) was cooled to −78° C. To the cooled solution, n-butyllithium (1.6 M in hexanes, 0.47 ml, 0.746 mmol) was added dropwise, and the reaction stirred at −78° C. for 45 minutes. A solution of the 3,4,5,6-tetrahydro-2H-[1,2']bipyridinyl-4-carboxylic acid methoxy-methyl-amide (0.124 g, 0.497 mmol) in anhydrous THF (3.0 ml) was then added dropwise to the reaction. The reaction stirred at −78° C. for 3 hours and at 0° C. until complete. The reaction was quenched at 0° C. by the addition of 1 N HCl (5 ml) and saturated NaHCO$_3$ (7.5 ml). The mixture was extracted with ethyl acetate, washed with brine, dried over MgSO$_4$, filtered, and concentrated. The crude product was purified by silica gel chromatography using 3-10% acetone in hexanes, yielding the product (0.1220 g, 71%) as a colorless oi: $^1$H NMR (400 MHz, CDCl$_3$) δ 8.16 (dd, J=4.9, 1.2 Hz, 1H), 7.81 (m, 2H), 7.61 (m, 2H), 7.46 (m, 1H), 6.67 (d, J=8.7 Hz, 1H), 6.59 (dd, J=6.7, 5.1 Hz, 1H). 4.33 (dt, J=13.1, 3.1 Hz, 2H), 3.42 (m, 1H), 3.14 (m, 2H), 1.93 (d, J=13.2, 2.2 Hz, 2H), 1.82 (m, 2H); $^{13}$C NMR (100 MHz, CDCl$_3$) 201.20, 159.20, 147.87, 137.53, 134.57, 132.28, 129.80, 128.20, 113.09, 107.34, 45.01, 43.76, 28.01; m/z calcd. for $C_{17}H_{17}BrN_2O$: 344.05 found: (M+H)$^+$347.1; HPLC retention time=3.205 min (wavelength 254 nm), purity=100%.

(3,4,5,6-Tetrahydro-2H-[1,2']bipyridinyl-4-yl)-(3'-trifluoromethyl-biphenyl-4-yl)-methanone In a vial, (4-bromo-phenyl)-(3,4,5,6-tetrahydro-2H-[1,2'] bipyridinyl-4-yl)-methanone (0.0634 g, 0.184 mmol) was taken up in DME (1.5 ml). To this solution, boronic acid (0.0846 g, 0.460 mmol), potassium phosphate (0.117 g, 0.551 mmol) and water (0.4 ml) were added. This mixture was then degassed using nitrogen. The tetrakis triphenylphosphine palladium (0.0213 g, 0.0184 mmol) was added, and the vial sealed. The reaction was then heated at 80° C. for 18 hours. After completion, 1 N NaOH solution was added and extraction twice with CH$_2$Cl$_2$ followed. The combined organic portions were washed with brine, dried, filtered, and concentrated. The crude product was purified by silica gel chromatography using 5-10% acetone in hexanes yielding the final product (0.042 g, 56%) as a white solid: $^1$H NMR (300 MHz, CDCl$_3$) δ 8.19 (dd, J=4.9, 1.2 Hz, 1H), 8.08 (d, J=8.5 Hz, 2H), 7.87 (s, 1H), 7.81 (d, J=7.5 Hz, 1H), 7.72 (d, J=8.5 Hz, 2H), 7.63 (m, 2H), 7.48 (m, 1H), 6.71 (d, J=8.6 Hz, 1H), 6.62 (dd, J=6.8, 5.2 Hz, 1H), 4.34 (dt, J=13.1, 3.0 Hz, 2H), 3.54 (m, 1H), 3.06 (m, 2H), 2.01 (dd, J=13.1, 2.5 Hz, 2H), 1.92 (dd, J=11.3, 4.0 Hz, 1H), 1.84 (m, 1H); m/z calcd. for $C_{24}H_{21}F_3N_2O$: 410.16 found: (M+H)$^+$ 411.05; HPLC retention time=3.313 min (wavelength 254 nm), purity=96.9%.

6.6. Preparation of (1-(Pyrimidin-2-yl)piperidin-4-yl)(4-4-trifluoromethylphenyl)-phenyl)methanone

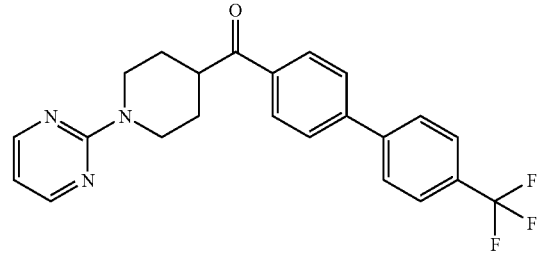 [SMILES: O=C(c1ccc(-c2ccc(C(F)(F)F)cc2)cc1)C1CCN(c2ncccn2)CC1]

The title compound was prepared from (4-bromophenyl) (1-(pyrimidin-2-yl)piperidin-4-yl)methanone as described below.

N-methoxy-N-methylpiperidine-4-carboxamide

A mixture of N-tert-butoxycarbonyl isonipecotic acid (1.50 g, 6.54 mmol, 1 eq), 1-(3-dimethylaminopropyl)3-ethylcarbodiimide hydrochloride (1.88 g, 9.81 mmol, 1.5 eq), 1-hydroxybenzotriazole (1.33 g, 9.81 mmol, 1.5 eq), and N,N-dimethylformamide (26 ml) was treated with N,N-diisopropylethylamine (4.60 ml, 26.2 mmol, 4 eq). The resultant yellow solution was stirred at room temperature for 5 minutes, and then N,O-dimethylhydroxylamine hydrochloride (766 mg, 7.85 mmol, 1.2 eq) was added, and stirring continued for 92 hours. The reaction mixture was diluted with 100 ml of ethyl acetate and washed sequentially with 1 N aq. NaOH, 1 N aq. HCl and brine. The organic phase was dried over $Na_2SO_4$ and concentrated to give an oil which was used with no further purification.

This oil was dissolved in 1:2 trifluoroacetic acid/dichloromethane (9 ml), and the reaction mixture was stirred at ambient temperature for 17 hours and then concentrated. Ether (30 ml) was added and the white solid which formed was collected by filtration, washed with ether and dried to afford 1.50 g (80% yield, 2 steps) of analytically pure product: 400 MHz $^1$H NMR ($d_6$-DMSO): 8.55 (br s, 1H), 8.25 (br s, 1H), 3.69 (s, 3H), 3.31 (m, 2H), 3.10 (s, 3H), 2.98 (m, 3H), 1.65-1.84 (m, 4H).

N-methoxy-N-methyl-1-(pyrimidin-2-yl)piperadine-4-carboxamide

A mixture of N-methoxy-N-methylpiperidine-4-carboxamide (1.50 g, 5.25 mmol, 1 eq), 2-chloropyrimidine (634 mg, 5.25 mmol, 1 eq), triethylamine (2.20 ml, 15.8 mmol, 3 eq), and ethanol (21 ml) was heated at 100° C. in a sealed tube for 19 hours. The reaction mixture was allowed to cool to room temperature and then concentrated. The residue was dissolved in dichloromethane, washed with water and brine, dried over $Na_2SO_4$, and concentrated. Column chromatography (silica gel, 50% 60% ethyl acetate/hexanes) gave 1.28 g (97% yield) of the product as a colorless oil: HPLC: 100% pure at 1.905 min (YMC-Pack ODS-A 4.6×33 mm column, 0% 100% solvent B over 4 min, 3 ml/min, 220 nm); LCMS (M+H)$^+$=251.05; 400 MHz $^1$H NMR (CDCl$_3$) 8.29 (d, J=4.7 Hz, 2H), 6.45 (t, J=4.7 Hz, 1H), 4.80 (m, 2H), 3.73 (s, 3H), 3.19 (s, 3H), 2.95 (m, 3H), 1.70-1.84 (m, 4H).

(4-Bromophenyl)(1-(pyrimidin-2-yl)piperidin-4-yl)methanone

A solution of 1,4-dibromobenzene (2.29 g, 9.72 mmol, 1.9 eq) in THF (20 ml) under $N_2$ was cooled to −78° C., and n-butyllithium (1.6 M in hexanes, 4.8 ml, 7.67 mmol, 1.5 eq) was added dropwise. The reaction mixture was stirred at −78° C. for 40 minutes, and a solution of N-methoxy-N-methyl-1-(pyrimidin-2-yl)piperadine-4-carboxamide (1.28 g, 5.11 mmol, 1 eq) in THF (5 ml) was added dropwise via a cannula. After 3 hours at −78° C., the reaction mixture was warmed to 0° C., stirred for 1 hour, and then quenched with 1 N aq. HCl (10 ml). The mixture was diluted with 150 ml of ethyl acetate, washed sequentially with saturated aq. $NaHCO_3$ and brine (75 ml each), and the organic phase was dried over $Na_2SO_4$ and concentrated. Column chromatography (silica gel, $CH_2Cl_2$ 3.5% ethyl acetate/$CH_2Cl_2$) afforded 1.47 g (83% yield) of the product as a pale yellow solid: HPLC: 99% pure at 3.748 min (YMC-Pack ODS-A 4.6×33 mm column, 0% 100% solvent B over 4 min, 3 ml/min, 220 nm); LCMS (M+H)$^+$=345.90; 400 MHz $^1$H NMR (CDCl$_3$) 8.31 (d, J=4.7 Hz, 2H), 7.83 (d, J=8.5 Hz, 2H), 7.63 (d, J=8.5 Hz, 2H), 6.48 (t, J=4.7 Hz, 1H), 4.81 (m, 2H), 3.49 (m, 1H), 3.08 (m, 2H), 1.72-1.95 (m, 4H).

(1-(Pyrimidin-2-yl)piperidin-4-yl)(4-4-trifluoromethylphenyl)-phenyl)methanone

A mixture of (4-bromophenyl)(1-(pyrimidin-2-yl)piperidin-4-yl)methanone (66 mg, 0.19 mmol, 1 eq), 4-trifluoromethylphenylboronic acid (91 mg, 0.47 mmol, 2.5 eq), potassium phosphate (122 mg, 0.57 mmol, 3 eq), and Pd(PPh$_3$)$_4$ (22 mg, 0.019 mmol, 0.1 eq) in 3:1 DME/water (2 ml) was heated at 80° C. under $N_2$ for 16 hours. The reaction mixture was cooled to room temperature, poured into 1 N NaOH, and extracted twice with dichloromethane. The combined organic layers were dried over $Na_2SO_4$ and concentrated. Column chromatography (silica gel, 25% ethyl acetate/hexanes) afforded 58 mg (73% yield) of the final product as a white solid: HPLC: 97% pure at 4.523 min (YMC-Pack ODS-A 4.6×33 mm column, 0% 100% solvent B over 4 min, 3 ml/min, 220 nm); LCMS (M+H)$^+$=412.20; 300 MHz $^1$H NMR (CDCl$_3$) 8.32 (d, J=4.7 Hz, 2H), 8.08 (d, J=8.4 Hz, 2H), 7.70-7.74 (m, 6H), 6.48 (t, J=4.7 Hz, 1H), 4.83 (m, 2H), 3.58 (m, 1H), 3.12 (m, 2H), 1.75-2.01 (m, 4H).

6.7. Preparation of (1-(Pyrimidin-2-yl)piperidin-4-yl)(4-4 trifluoromethylphenyl)-phenyl)methanol

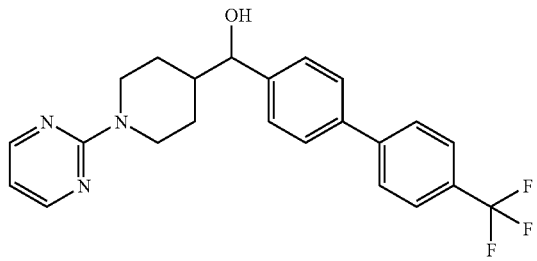 [SMILES: OC(c1ccc(-c2ccc(C(F)(F)F)cc2)cc1)C1CCN(c2ncccn2)CC1]

Sodium borohydride (3.0 mg, 0.080 mmol, 1.5 eq) was added to a solution of (1-(pyrimidin-2-yl)piperidin-4-yl)(4-4-trifluoromethylphenyl)phenyl)methanone (22 mg, 0.053 mmol, 1 eq) in 1:1 methanol/dichloromethane. The reaction mixture was stirred at room temperature for 1 hour and then slowly quenched with saturated aq. NaHCO$_3$. The biphasic mixture was extracted twice with dichloromethane, and the combined organic layers were dried over Na$_2$SO$_4$ and concentrated. Preparative TLC (500 m silica gel, 33% ethyl acetate/hexanes) gave 17 mg (77% yield) of the product as a white solid: HPLC: 100% pure at 4.285 min (YMC-Pack ODS-A 4.6×33 mm column, 0% 100% solvent B over 4 min, 3 ml/min, 220 nm); LCMS (M+H)$^+$=414.10; 300 MHz $^1$H NMR (CDCl$_3$) 8.27 (d, J=4.7 Hz, 2H), 7.69 (s, 4H), 7.59 (d, J=8.3 Hz, 2H), 7.42 (d, J=8.2 Hz, 2H), 6.43 (t, J=4.7 Hz, 1H), 4.71-4.87 (m, 2H), 4.48 (m, 1H), 2.72-2.89 (m, 2H), 1.88-2.11 (m, 3H), 1.19-1.49 (m, 3H).

6.8. Preparation of Biphenyl-4-yl-(1-pyrimidin-2-yl-1,2,3,6-tetrahydro-pyridin-4-yl)-methanone

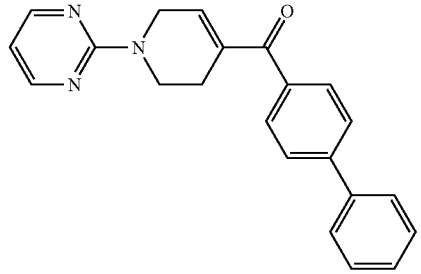 [SMILES: O=C(C1=CCN(c2ncccn2)CC1)c1ccc(-c2ccccc2)cc1]

To a solution of 2-chloropyrimidine (300 mg, 2.619 mmol) in dioxane (5 ml), was added piperidin-4-one hydrochloride monohydrate (402.3 mg, 2.619 mmol) at room temperature. The mixture was heated at 80° C. overnight and concentrated under reduced pressure. The residue was treated with EtOAc (30 ml) and saturated NaHCO$_3$ (10 ml). After separation of the layers, the aqueous phase was extracted with EtOAc (2×10 ml). The combined organic layers were washed with brine (10 ml), dried (MgSO$_4$), filtered, and concentrated under reduced pressure to furnish a crude product. This material was purified by column chromatography (40% EtOAc/hexanes) to give 1-pyrimidin-2-yl-piperidin-4-one (320 mg, 53%) as an off-white solid: $^1$H NMR (CDCl$_3$, 400 MHz) δ 8.38 (d, J=6.4 Hz, 2H), 6.61 (t, J=6.4 Hz, 9H), 4.16 (t, J=5.6 Hz, 2H), 2.53 (t, J=5.6 Hz, 2H).

To a solution of LDA (prepared from diisopropylamine (167.4 mg, 1.658 mmol) and n-BuLi (2.5 M in hexanes, 0.663 ml, 1.658 mmol) at −78° C., was added a solution of the above 1-pyrimidin-2-yl-piperidin-4-one (320 mg, 1.382 mmol). The mixture was stirred at the same temperature for 1 hour, followed by the addition of PhNTf$_2$ (543.1 mg, 1.52 mmol). The reaction mixture was warmed up to room temperature and stirred for 3 hours before it was quenched with the addition of saturated ammonium chloride (15 ml) and EtOAc (40 ml). After separation of the layers, the aqueous phase was extracted with EtOAc (2×10 ml). The combined organic layers were washed with brine (10 ml), dried (MgSO$_4$), filtered, and concentrated under reduced pressure to furnish the crude product. This material was purified by column chromatography (20% EtOAc/hexanes) to give the corresponding triflate (210.7 mg, 49%) as a white solid as long with recovered starting material (142.9 mg): $^1$H NMR (CDCl$_3$, 400 MHz) δ 8.37 (d, J=6.4 Hz, 2H), 6.59 (t, J=6.4 Hz, 1H), 5.91 (m, 1H), 4.41 (m, 2H), 4.11 (t, J=5.6 Hz, 2H), 2.55 (m, 2H); MS calc'd for C$_{10}$H$_{11}$F$_3$N$_3$O$_3$S [M+H]$^+$: 310; Found: 310.

To a solution of the above triflate (210.7 mg, 0.682 mmol) in methanol (10 ml), was added Pd(OAc)$_2$ (10.7 mg, 0.047 mmol), PPh$_3$ (31.3 mg, 0.119 mmol) and diisopropyl ethylamine (352.6 mg, 2.728 mmol) at room temperature. Carbon monoxide was bubbled through the solution for 4 hours before the mixture was concentrated under reduced pressure. The residue was treated with EtOAc (30 ml) and water (10 ml). The aqueous phase was further extracted with EtOAc (2×10 ml). The combined organic layers were washed with brine (10 ml), dried (MgSO$_4$), filtered, and concentrated under reduced pressure to furnish the crude product. This material was purified by column chromatography (30% EtOAc/hexanes) to give 1-pyrimidin-2-yl-1,2,3,6-tetrahydro-pyridin-4-carboxylic acid methyl ester (73.8 mg, 50%) as white crystals: $^1$H NMR (CDCl$_3$, 400 MHz) δ 8.37 (d, J=6.4 Hz, 2H), 7.04 (m, 1H), 6.54 (t, J=6.4 Hz, 1H), 4.41 (m, 2H), 3.98 (t, J=5.6 Hz, 2H), 3.79 (s, 3H), 2.52 (m, 2H).

To a suspension of 1-pyrimidin-2-yl-1,2,3,6-tetrahydro-pyridin-4-carboxylic acid methyl ester (73.8 mg, 0.337 mmol) and N-methyl-O-methyl hydroxylamine hydrochloride (51.0 mg, 0.552 mmol) in THF (3 ml), was added isopropyl magnesium chloride (2.0 M in THF, 0.505 ml) at −20° C. over 15 minute-period. The mixture was stirred at −10° C. for another 30 minutes before it was quenched with the addition of saturated ammonium chloride (10 ml). The mixture was extracted with EtOAc (2×15 ml). The combined organic layers were washed with brine (15 ml), dried (MgSO$_4$), filtered, and concentrated under reduced pressure to furnish the crude product. This material was purified by column chromatography (4% MeOH/CH$_2$Cl$_2$) to give 1-pyrimidin-2-yl-1,2,3,6-tetrahydro-pyridin-4-carboxylic acid methoxy-methyl amide (48 mg, 58%) as white crystals: $^1$H NMR (CDCl$_3$, 400 MHz) δ 8.35 (d, J=6.4 Hz, 2H), 6.53 (t, J=6.4 Hz, 1H), 6.43 (m, 1H), 4.35 (m, 2H), 3.99 (t, J=5.6 Hz, 2H), 3.66 (s, 3H), 3.27 (s, 3H), 2.55 (m, 2H).

To a solution of 1-pyrimidin-2-yl-1,2,3,6-tetrahydro-pyridin-4-carboxylic acid methoxy-methyl amide (48 mg, 0.196 mmol) in THF (1 ml), was added 1-biphenyl-4-yl magnesium bromide (0.5 M in THF) at 0° C. The mixture was stirred at this temperature for 1 hour and quenched with addition of water (5 ml) and EtOAc (20 ml). The aqueous phase was further extracted with EtOAc (2×8 ml). The combined organic layers were washed with brine (5 ml), dried (MgSO$_4$), filtered, and concentrated under reduced pressure to furnish the crude product. This material was purified by column chromatography (4% MeOH/CH$_2$Cl$_2$) to give the title compound (20 mg, 30%) as an off-white solid: $^1$H NMR (CDCl$_3$, 400 MHz) δ 8.38 (d, J=6.4 Hz, 2H), 7.82-7.42 (m, 9H), 6.70 (m, 1H), 6.58 (t, J=6.4 Hz, 1H), 4.51 (m, 2H), 4.13 (t, J=5.6 Hz, 2H), 2.72 (m, 2H); MS calc'd for C$_{22}$H$_{20}$N$_3$O [M+H]$^+$: 342; Found: 342.

6.9. Preparation of Biphenyl-4-yl-(1-pyrimidin-2-yl-1,2,3,6-tetrahydro-pyridin-4-yl)-methanol

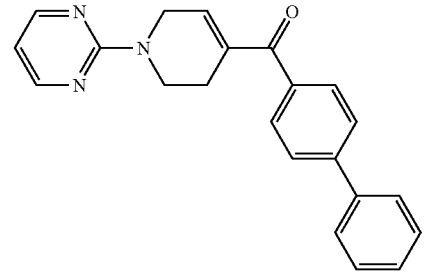 [SMILES: O=C(C1=CCN(c2ncccn2)CC1)c1ccc(-c2ccccc2)cc1]

To a solution of biphenyl-4-yl-(1-pyrimidin-2-yl-1,2,3,6-tetrahydro-pyridin-4-yl)-methanone (12.2 mg, 0.0355 mmol) in methanol (0.5 ml), was added CeCl$_3$ heptahydrate (13.2 mg, 0.0355 mmol) and sodium borohydride (1.5 mg, 0.0355 mmol) at room temperature. The mixture was stirred for 1 hour and diluted with EtOAc (10 ml). The mixture was washed with water (5 ml), brine (5 ml), dried (MgSO$_4$), filtered, and concentrated under reduced pressure to furnish the crude product. This material was purified by column chromatography (6% MeOH/CH$_2$Cl$_2$) to give the title compound (12 mg, 98%) as a white gel: $^1$H NMR (CDCl$_3$, 400 MHz) δ 8.36 (d, J=6.4 Hz, 2H), 7.62-7.37 (m, 9H), 6.46 (t, J=6.4 Hz, 1H), 6.02 (m, 1H), 5.24 (m, 1H), 4.31 (m, 2H), 3.96 (m, 1H), 3.83 (m, 1H), 2.14 (m, 2H); MS calc'd for C$_{22}$H$_{22}$N$_3$O [M+H]$^+$: 344; Found: 344.

6.10. Preparation of 2-[4-(Biphenyl-4-yloxy)-piperidin-1-yl]-pyrimidine

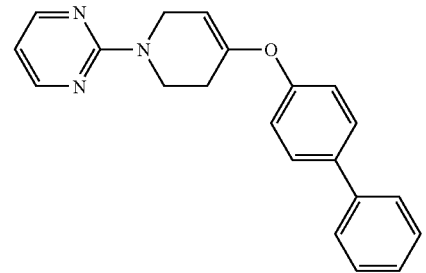 [SMILES: C1=C(Oc2ccc(-c3ccccc3)cc2)CCN(c2ncccn2)C1]

To a solution of 1-pyrimidin-2-yl-piperidin-4-one (50 mg, 0.282 mmol) in methanol (0.8 ml), was added sodium borohydride (12.0 mg, 0.282 mmol) at room temperature. After being stirred for 10 minutes, the mixture was treated with EtOAc (10 ml) and water (3 ml). The organic layer was washed with brine (2 ml), dried (MgSO$_4$), filtered, and concentrated under reduced pressure to furnish the crude product. This material was purified by column chromatography (20% EtOAc/hexanes) to give the corresponding alcohol (51 mg, 100%) as a white solid.

To a mixture of the above alcohol (50 mg, 0.279 mmol), PPh$_3$ (109.6 mg, 0.418 mmol) and biphenyl-4-ol (57.0 mg, 0.335 mmol) in THF (3 ml), was added DEAD (40% in toluene, 0.152 ml, 0.335 mmol) at 0° C. After being stirred overnight, the mixture was treated with EtOAc (15 ml) and water (5 ml). The aqueous phase was extracted with EtOAc (2×5 ml). The combined organic layers were washed with brine (5 ml), dried (MgSO$_4$), filtered, and concentrated under reduced pressure to furnish the crude product. This material was purified by column chromatography (15% EtOAc/hexanes) to give the title compound (81 mg, 88%) as white crystals: $^1$H NMR (CDCl$_3$, 400 MHz) δ 8.38 (d, J=6.4 Hz, 2H), 7.59-7.04 (m, 9H), 6.61 (t, J=6.4 Hz, 1H), 4.62 (m, 1H), 4.21 (m, 2H), 3.68 (m, 2H), 2.14 (m, 2H), 1.83 (m, 2H); MS calc'd for C$_{21}$H$_{22}$N$_3$O [M+H]$^+$: 332; Found: 332.

6.11. Preparation of (3'-Chloro-biphenyl-4-yl)-(4-thiazol-2-yl-piperazin-1-yl)-methanone

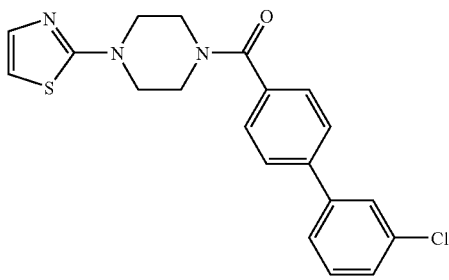 [SMILES: O=C(c1ccc(-c2cccc(Cl)c2)cc1)N1CCN(c2nccs2)CC1]

To a solution of 1-(thiazol-2-yl)piperazine (ca. 0.915 mmol, prepared from 150 mg 2-bromothiazole according to the methods described in Astles et al., *J. Med. Chem.*, 39: 1423-1432 (1996)), 3'-chloro-biphenyl-4-carboxylic acid (212.9 mg, 0.915 mmol) in CH$_2$Cl$_2$ (4 ml), was added EDC (209.7 mg, 1.098 mmol) and HOBt (148.2 mg, 1.098 mmol). After being stirred overnight, the mixture was treated with EtOAc (50 ml) and water (15 ml). The organic phase was washed with brine (5 ml), dried (MgSO$_4$), filtered, and concentrated under reduced pressure to furnish the crude product. This material was purified by column chromatography (20% acetone/hexanes) to give the title compound (225 mg, 64% for two steps) as a white solid: $^1$H NMR (CDCl$_3$, 400 MHz) δ 7.64-7.23 (m, 9H), 6.65 (t, J=3.6 Hz, 1H), 4.92 (m, br, 2H), 3.57 (m, br, 6H), 3.68 (m, 2H), 2.14 (m, 2H), 1.83 (m, 2H); MS calc'd for C$_{20}$H$_{19}$ClN$_3$OS [M+H]$^+$: 384; Found: 384.

6.12. Preparation of 4-(4'-Chloro-biphenyl-4-yl)-1-pyrimidin-2-yl-piperidin-4-ol

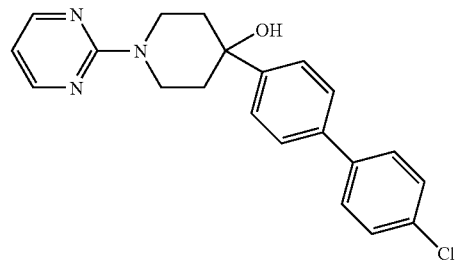 [SMILES: OC1(c2ccc(-c3ccc(Cl)cc3)cc2)CCN(c2ncccn2)CC1]

To a solution of 1,4-dibromobenzene (213.3 mg, 0.904 mmol) in THF (4 ml), was added n-BuLi (2.5 M in hexanes, 0.362 ml, 0.904 mmol) at −78° C. After being stirred for 30 minutes at the same temperature, a solution of 1-pyrimidin-2-yl-piperidin-4-one (80 mg, 0.452 mmol) in THF (3 ml) was added. The mixture was allowed to warm to room temperature and stirred for 1 hour. The reaction was quenched with addition of water (10 ml) and EtOAc (50 ml). The organic layer was washed with brine (5 ml), dried (MgSO$_4$), filtered, and concentrated under reduced pressure to furnish the crude product. This material was purified by column chromatography (40% EtOAc/hexanes) to give 4-(4-Bromo-phenyl)-1-pyrimidin-2-yl-piperidin-4-ol as a colorless oil (140 mg, 93%): $^1$H NMR (CDCl$_3$, 400 MHz) δ 8.33 (d, J=6.4 Hz, 2H), 7.47 (d, J=12.0 Hz, 2H), 7.41 (d, J=12.0 Hz, 2H), 6.49 (t, J=6.4 Hz, 1H), 4.72 (m, 2H), 3.40 (m, 2H), 2.05 (m, 2H), 1.78 (m, 2H); MS calc'd for C$_{15}$H$_{17}$BrN$_3$O [M+H]$^+$: 335; Found: 335.

Following the general procedures for the Suzuki reactions, the title compound was prepared in 61% yield as a colorless glass: $^1$H NMR (CDCl$_3$, 400 MHz) δ 8.35 (d, J=6.4 Hz, 2H), 7.59-7.37 (m, 8H), 6.50 (t, J=6.4 Hz, 1H), 4.73 (m, 2H), 3.46 (t, J=12.4 Hz, 2H), 2.15 (m, 2H), 1.88 (m, 2H); MS calc'd for C$_{21}$H$_{21}$ClN$_3$O [M+H]$^+$: 366; Found: 366.

6.13. Preparation of Biphenyl-4-yl-(1-pyrimidin-2-yl-azetidin-3-yl)-methanone

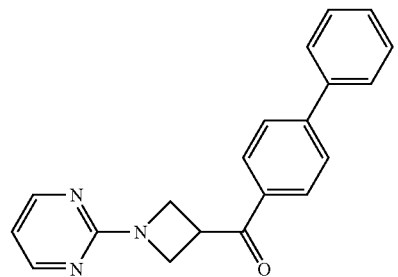 [SMILES: O=C(c1ccc(-c2ccccc2)cc1)C1CN(c2ncccn2)C1]

To a stirred solution of 3-azetidine carboxylic acid methyl ester hydrochloride (150 mg, 0.99 mmol) and 2-chloropyrimidine (113.4 mg, 0.99 mmol) in methanol, was added TEA (200 mg, 1.98 mmol) at room temperature. The mixture was stirred at 50° C. for 5 hours and concentrated under reduced pressure. The residue was suspended in EtOAc (50 ml) and washed with water (15 ml), brine (5 ml), dried (MgSO$_4$), filtered, and concentrated under reduced pressure to furnish the crude product. This material was purified by column chromatography (40% EtOAc/hexanes) to give 1-pyrimidin-2-yl-azetidine-3-carboxylic acid methyl ester as a light yellow solid (137.3 mg, 72%): $^1$H NMR (CDCl$_3$, 400 MHz) δ 8.37 (d, J=6.4 Hz, 2H), 6.58 (t, J=6.4 Hz, 1H), 4.30 (m, 4H), 3.77 (s, 3H), 3.56 (m, 1H).

To a suspension of the above ester (137.3 mg, 0.711 mmol) and N-methyl-O-methyl hydroxylamine hydrochloride (127.6 mg, 1.103 mmol) in THF (5 ml), was added iso-propyl magnesium chloride (2.0 M in THF, 1.067 ml, 2.133 mmol) at −20° C. during 15 minutes. The mixture was stirred at −10° C. for another 30 minutes before it was quenched with the addition of saturated ammonium chloride (10 ml). The mixture was extracted with EtOAc (2×15 ml). The combined organic layers were washed with brine (10 ml), dried (MgSO$_4$), filtered, and concentrated under reduced pressure to furnish the crude product. This material was purified by column chromatography (4% MeOH/CH$_2$Cl$_2$) to give 1-pyrimidin-2-yl-azetidine-3-carboxylic acid methoxy-methyl-amide (385.9 mg, 98%) as a white solid: $^1$H NMR (CDCl$_3$, 400 MHz) δ 8.32 (d, J=6.4 Hz, 2H), 6.55 (t, J=6.4 Hz, 1H), 4.34 (m, 4H), 3.88 (m, 1H), 3.70 (s, 3H), 3.23 (s, 3H).

To a solution of the above amide (50 mg, 0.225 mmol) in THF (1 ml), was added 4-biphenyl magnesium chloride (0.5 M in THF, 0.9 ml, 0.45 mmol) at −78° C. The mixture was slowly warmed up to room temperature and stirred for 2 hours before quenched with addition of water (10 ml) and EtOAc (30 ml). The organic layer was separated and washed with brine (5 ml), dried (MgSO$_4$), filtered, and concentrated under reduced pressure to furnish the crude product. This material was purified by column chromatography (3% MeOH/CH$_2$Cl$_2$) to furnish the title compound (21 mg, 30%) as white crystals: $^1$H NMR (CDCl$_3$, 400 MHz) δ 8.33 (d, J=6.4 Hz, 2H), 7.98-7.43 (m, 9H), 6.58 (t, J=6.4 Hz, 1H), 4.45 (m, 4H), 4.38 (m, 1H); MS Calc'd for C$_{20}$H$_{18}$N$_3$O [M+H]$^+$: 316; Found: 316.

6.14. Preparation of (3'-Chloro-biphenyl-4-yl)-(1-pyrimidin-2-yl-pyrrolidin-3-yl)-methanone

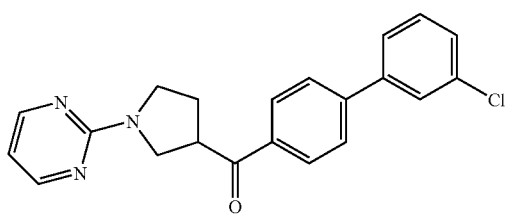 [SMILES: O=C(c1ccc(-c2cccc(Cl)c2)cc1)C1CCN(c2ncccn2)C1]

To a solution of N-Boc-β-proline (400 mg, 1.858 mmol), EDC (425.9 mg, 2.23 mmol) and HOBt (326.1 mg, 2.415 mmol) in methylene chloride (8 ml), was added N-methyl-O-methyl hydroxylamine hydrochloride (217.5 mg, 2.23 mmol) and TEA (281.5 mg, 2.787 mmol) at 0° C. After stirring overnight, the mixture was treated with EtOAc (80 ml) and water (15 ml). The organic phase was washed with brine (15 ml), dried (MgSO$_4$), filtered, and concentrated under reduced pressure to furnish the crude product.

To a solution of the above crude ester in methylene chloride (4 ml), was added dropwise TFA (4 ml) at room temperature. The mixture was stirred for 40 minutes and concentrated under reduced pressure to generate the crude product as the TFA salt.

To a mixture of the above product and 2-chloropyrimidine (212.8 mg, 1.858 mmol) in dioxane (7 ml) was added TEA (563 mg, 5.574 mmol). The mixture was heated at 80° C. for 4 hours, and was concentrated under reduced pressure. The residue was treated with water (20 ml) and EtOAc (60 ml). After separation of the layers, the aqueous phase was further extracted with EtOAc (20 ml). The combined organic layers were washed with brine (10 ml), dried (MgSO$_4$), filtered, and concentrated under reduced pressure to furnish the crude product. This material was purified by column chromatography (40% acetone/hexanes) to furnish 1-pyrimidin-2-yl-pyrrolidine-3-carboxylic acid methoxy-methyl-amide (203.8 mg, 47% for three steps) as an off-white solid: $^1$H NMR (CDCl$_3$, 400 MHz) δ 8.34 (d, J=6.4 Hz, 2H), 6.50 (t, J=6.4 Hz, 1H), 3.94 (m, 1H), 3.82 (m, 1H), 3.75 (s, 3H), 3.70 (m, 1H), 3.65 (m, 1H), 3.63 (m, 1H), 3.23 (s, 3H), 2.33 (m, 3H), 2.23 (m, 1H).

To a solution of 1,4-dibromobenzene (407.5 mg, 1.727 mmol) in THF (6 ml) was added n-BuLi (2.5 M in hexanes, 0.691 ml, 1.727 mmol) at −78° C. The mixture was stirred at the temperature for 30 minutes before the addition of a solution of the above amide (203.8 mg, 0.8636 mmol) in THF (4 ml). After stirring at −78° C. for 30 minutes, the mixture was warmed to room temperature for 1 hour. EtOAc (40 ml) and water (15 ml) was added to the reaction, followed by separation of the layers. The aqueous phase was extracted with EtOAc (15 ml). The combined organic layers were washed with brine (10 ml), dried (MgSO$_4$), filtered, and concentrated under reduced pressure to furnish the crude product. This material was purified by column chromatography (40% acetone/hexanes) to furnish (4-bromo-phenyl)-(1-pyrimidin-2-yl-pyrrolidin-3-yl)-methanone (182.2 mg, 64%) as an off-white solid: $^1$H NMR (CDCl$_3$, 400 MHz) δ 8.32 (d, J=6.4 Hz, 2H), 7.87 (d, J=12.0 Hz, 2H), 7.63 (d, J=12.0 Hz, 2H), 6.51 (t, J=6.4 Hz, 1H), 4.07 (m, 1H), 3.98 (m, 1H), 3.86 (m, 1H), 3.74 (m, 2H), 2.38 (m, 2H).

Following the general procedures for the Suzuki reactions, the title compound was prepared in 63% as a pale yellow solid: $^1$H NMR (CDCl$_3$, 400 MHz) δ 8.38 (d, J=6.4 Hz, 2H), 8.11-7.42 (m, 8H), 6.53 (t, J=6.4 Hz, 1H), 4.19 (m, 1H), 4.04 (m, 1H), 3.84 (m, 1H), 3.77 (m, 2H), 2.42 (m, 1H), 2.38 (m, 1H); MS Calc'd for C$_{21}$H$_{19}$ClN$_3$O [M+H]$^+$: 364; Found: 364.

6.15. Preparation of (4-Pyrimidin-2-yl-homopiperazin-1-yl)[4-(3-trifluoromethylphenyl-phenyl]-methanone

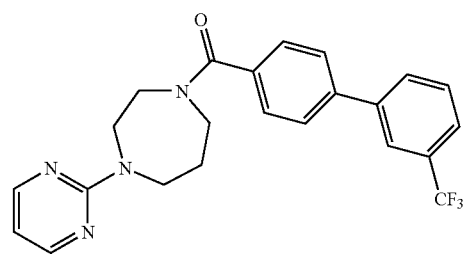 [SMILES: O=C(c1ccc(-c2cccc(C(F)(F)F)c2)cc1)N1CCCN(c2ncccn2)CC1]

The title compound was prepared from 1-(2-pyrimidyl)-homopiperazine as described below.

1-(2-Pyrimidyl)-homopiperazine

To a solution of homopiperazine (3.5 g, 35 mmol) in ethanol (100 ml) at 40° C., was added portionwise 2-chloropyrimidine (2.0 g, 17.5 mmol). The mixture was stirred for 1 hour then concentrated in vacuo. The residue was dissolved in methylene chloride (75 ml) and washed with a saturated solution of sodium bicarbonate and brine. Layers were separated, and the organic layer was dried over magnesium sulfate and concentrated. The resulting residue was purified by flash chromatography and a semi-solid (1.0 g) was collected and used as is.

(4-Pyrimidin-2-yl-homopiperazin-1-yl)-[4-(3-trifluoromethylphenylphenyl]-methanone To a solution of 3-trifluoromethyl-biphenyl-4-carboxylic acid (0.38 g, 1.41 mmol) and 1-(2-pyrimidyl)-homopiperazine (0.25 g, 1.41 mmol) in methylene chloride (20 ml), was added EDCl (0.27 g, 1.41 mmol) and HOAt (0.19 g, 1.41 mmol) triethylamine (0.20 ml, 1.41 mmol). The mixture was stirred for 16 hours and then washed with brine. The layers were separated, and the organic phase was dried over magnesium sulfate and concentrated. The resulting oil was purified by flash chromatography and a clear oil was collected. The oil was dissolved in a minimal amount of t-butylmethylether, and crystals were formed collected (0.20 g). Spectral data was consistent with structure. MS (M+1)=427. HPLC (>95%). $^1$H NMR (CDCl3) 8.35 (m, 2H), 7.55 (m, 8H), 6.58 (t, 1H), 3.87 (bm, 8H), 1.92 (m, 2H).

6.16. Preparation of (3'-Chloro-biphenyl-4-yl)-(5-pyrimidin-2-yl-hexahydro-pyrrolo[3,4-c]pyrrol-2-yl)-methanone

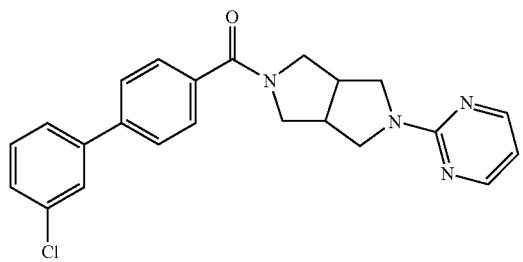 [SMILES: O=C(c1ccc(-c2cccc(Cl)c2)cc1)N1CC2CN(c3ncccn3)CC2C1]

The title compound was prepared from 5-pyrimidin-2-yl-hexahydro-pyrrolo[3,4-c]pyrrole-2-carboxylic acid tert-butyl ester as described below.

5-Pyrimidin-2-yl-hexahydro-pyrrolo[3,4-c]pyrrole-2-carboxylic acid tert-butyl ester A solution of hexahydro-pyrrolo[3,4-c]pyrrole-2-carboxylic acid tert-butyl ester (1.0 g, 4.7 mmol), 2-chloropyrimidine (0.54 g, 4.7 mmol), triethylamine (2 ml, 14 mmol) and ethyl alcohol (25 ml) was maintained at reflux for 4 hours. The solution was then cooled to room temperature and concentrated to afford a solid residue that was dissolved in dichloromethane ($CH_2Cl_2$), which was washed sequentially with sat. aq. sodium bicarbonate and brine, dried ($Na_2SO_4$), filtered, and concentrated to afford 0.82 g (60%) of the product as an orange solid: $^1$H NMR (400 MHz, $CDCl_3$): δ 8.34 (d, J=4.8 Hz, 2H), 6.53 (t, J=4.8 Hz, 1H), 3.86-3.79 (m, 2H), 3.72-3.62 (m, 2H), 3.57-3.50 (m, 2H), 3.41-3.33 (m, 1H), 3.33-3.26 (m, 1H), 3.05-2.96 (m, 2H), 1.47 (s, 9H); LRMS m/z 291 (M+H)$^+$.

(3'-Chloro-biphenyl-4-yl)-(5-Pyrimidin-2-yl-hexahydro-pyrrolo[3,4-c]pyrrol-2-yl)-methanone A solution of 5-pyrimidin-2-yl-hexahydro-pyrrolo[3,4-c] pyrrole-2-carboxylic acid tert-butyl ester (0.70 g, 2.4 mmol) and $CH_2Cl_2$ (20 ml) was treated with trifluoroacetic acid (TFA, 10 ml) and maintained at room temperature for 3 hours. The resulting solution was concentrated, and the residue was dissolved in $CH_2Cl_2$ (5 ml) and added to a solution of 3-chloro-biphenyl-4-yl-carboxylic acid (0.62 g, 2.6 mmol), O-(7-Azabenzotriazol-1-yl)-N,N,N',N'-tetramethyluronium-hexafluorophosphate (HATU, 1.0 g, 2.6 mmol), diisopropyl-ethylamine (1.5 ml, 8 mmol), and $CH_2Cl_2$ (20 ml). The resulting solution was maintained at room temperature for 2 hours, diluted with EtOAc, washed with sat. aq. $NaHCO_3$ and brine, dried ($MgSO_4$), filtered, and concentrated. The solid residue was recrystallized from methyl alcohol to afford the final product as white needles: $^1$H NMR ($CD_3OD$): δ 8.32 (d, J=4.8 Hz, 2H), 7.71 (d, J=8.5 Hz, 2H), 7.67 (s, 1H), 7.63 (d, J=8.5 Hz, 2H), 7.60-7.50 (m, 1H), 7.45 (t, J=7.9 Hz, 1H), 7.40-7.37 (m, 1H), 6.63 (t, J=4.8 Hz, 1H), 3.96 (dd, J=7.8, 12.8 Hz, 1H), 3.86 (ddd, J=3.0, 7.2, 10.6 Hz, 2H), 3.76 (dd, J=7.5, 11.6 Hz, 1H), 3.65-3.58 (m, 2H), 3.51 (dd, J=5.1, 11.3 Hz, 1H), 3.43 (dd, J=4.7, 11.7 Hz, 1H), 3.21-3.07 (m, 2H). $^{13}$C NMR (100 MHz, $CD_3OD$): δ 171.8, 161.4, 159.1, 143.5, 142.9, 137.0, 136.0, 131.6, 129.0, 128.2, 128.1, 126.6, 110.9, 54.5, 51.9, 51.7, 51.1, 43.9, 42.0; LRMS m/z 405 (M+H)$^+$; Anal. calcd for $C_{23}H_{21}ClN_4O$: C, 68.23; H, 5.23; N, 13.84. Found: C, 68.01; H, 5.23; N, 13.60.

6.17. Preparation of (2',4'-Difluoro-biphenyl-4-yl)-(8-pyrimidin-2-yl-8-aza-bicyclo[3.2.1]oct-3-yl)-methanone

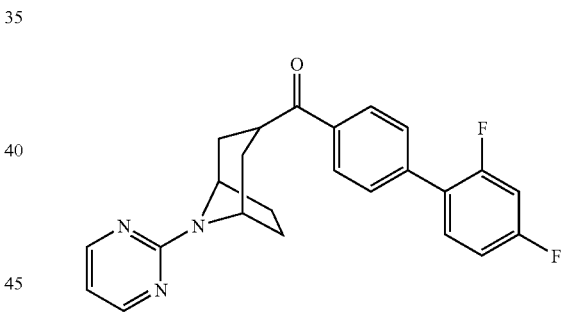

The title compound was prepared as follows.

8-Pyrimidin-2-yl-8-aza-bicyclo[3.2.1]octan-3-one

A solution of 8-aza-bicyclo[3.2.1]octan-3-one hydrochloric acid (5.0 g, 30.9 mmol), 2-chloro-pyrimidine (4.95 g, 43.2 mmol), $NaHCO_3$ (7.78 g, 92.7 mmol) and isopropanol (200 ml) was maintained at reflux over weekend. The resulting reaction mixture was concentrated and purified by ISCO to afford 8-pyrimidin-2-yl-8-aza-bicyclo[3.2.1]octan-3-one (4.0 g, 52.9%) as a white solid: MS (M+1)=204. $^1$H NMR (MeOH) 8.36 (d, J=12 Hz 2H), 6.75 (m, 1H), 4.97 (m, 2H), 2.75 (d, J=12 Hz, 1H), 2.71 (d, J=12 Hz, 1H), 2.32 (d, J=50 Hz, 2H), 2.22 (m, 2H), 1.87 (m, 2H).

3-[(4-Bromo-phenyl)-methoxy-methylene]-8-pyrimidin-2-yl-8-aza-bicyclo[3.2.1]octane To a solution of [(4-bromo-phenyl)-methoxy-methyl]-phosphonic acid diethyl ester (4.58 g, 13.5 mmol) in 1,2- dimethoxy-ethane (60 ml), was added NaH (540 mg, 13.5 mmol, 60% in mineral oil) in one portion. The mixture was stirred at 50° C. for 1.5 hrs before it was added by 8-pyrimidin-2-yl-8-aza-bicyclo[3.2.1]octan-3-one (2.0 g, 9.85 mmol) in 1,2-dimethoxy-ethane (5 ml). The mixture was stirred at 50° C. over the weekend. The resulting mixture was concentrated down and purified by ISCO to afford 3-[(4-bromo-phenyl)-methoxy-methylene]-8-pyrimidin-2-yl-8-aza-bicyclo[3.2.1]octane (600 mg, 30%). The white solid product was used as it was. MS (M+1)=386.

(4-Bromo-phenyl)-(8-pyrimidin-2-yl-8-aza-bicyclo[3.2.1]oct-3-yl)-methanone

A solution of 3-[(4-bromo-phenyl)-methoxy-methylene]-8-pyrimidin-2-yl-8-aza-bicyclo[3.2.1]octane (2.44 g, 6.32 mmol), aqueous HCl (10.5 ml, 6N) and THF (50 ml) was stirred at room temperature overnight. The mixture was added by saturated aq. NaHCO$_3$ until bubbling was gone. The mixture was diluted with ethyl acetate and the organic phase was dried over MgSO$_4$ and concentrated. ISCO was used to do purification and (4-bromo-phenyl)-(8-pyrimidin-2-yl-8-aza-bicyclo[3.2.1]oct-3-yl)-methanone was obtained as white solid (2.16 g, 92%). MS (M+1)=374. $^1$H NMR (CDCl$_3$) 8.33 (d, J=12 Hz 2H), 7.84 (d, J=13 Hz 2H), 7.62 (d, J=13 Hz 2H), 6.51 (t, J=12 Hz 1H), 4.87 (m, 2H), 3.90 (m, 1H), 2.23 (m, 2H), 2.08 (m, 2H), 1.97 (m, 2H), 1.72 (m, 2H).

(2,4-Difluoro-biphenyl-4-yl)-(8-pyrimidin-2-yl-8-aza-bicyclo[3.2.1]oct-3-yl)-methanone A solution of (4-bromo-phenyl)-(8-pyrimidin-2-yl-8-aza-bicyclo[3.2.1]oct-3-yl)-methanone (250 mg, 0.92 mmol), 2,4-di-fluoro-phenylboronic acid (290 mg, 1.84 mmol), [1,1-bis(diphenylphosphino)ferrocene]dichloropalladium(II), complex with dichloromethane (1:1) (67 mg, 0.092 mmol), K$_3$PO$_4$(390 mg, 1.84 mmol), 2-dimethoxy-ethane (5 ml) and water (1.6 ml) was stirred at 80° C. for one hour. The reaction mixture was diluted with ethyl acetate and 1N NaOH solution. The organic layer was dried by MgSO$_4$ and concentrated. ISCO was used for purification, and the product was obtained as a white solid (2',4'-difluoro-biphenyl-4-yl)-(8-pyrimidin-2-yl-8-aza-bicyclo[3.2.1]oct-3-yl)-methanone (69.6 mg, 19%). MS (M+1)=406. $^1$H NMR (CDCl$_3$) 8.34 (d, J=12 Hz 2H), 8.00 (d, J=21 Hz 2H), 7.62 (dd, J=19 Hz, 4 Hz, 2H), 7.45 (m, 1H), 6.99 (m, 2H), 6.52 (t, J=12 Hz, 1H), 4.90 (m, 2H), 4.00 (m, 1H), 2.25 (m, 2H), 2.12 (m, 2H), 2.02 (m, 2H), 1.78 (m, 2H).

6.18. Preparation of (3-(Pyrimidin-2-yl)-3,8-diaza-bioiclo[3.2.1]octan-8-yl)(3'-(trifluoromethyl)biphenyl-4-yl)methanone

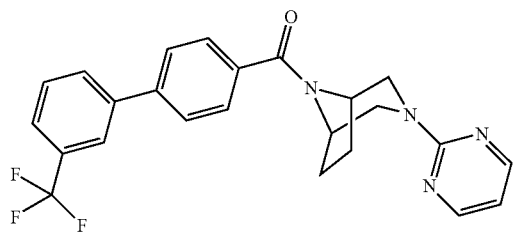 [SMILES: O=C(c1ccc(-c2cccc(C(F)(F)F)c2)cc1)N1C2CCC1CN(c1ncccn1)C2]

The title compound was prepared as follows.

3-Pyrimidin-2-yl-3,8-diaza-bicyclo[3.2.1]octane-8-carboxylic acid tert-butyl ester A solution of 3,8-diaza-bicyclo[3,2,1]octane-8-carboxyli acid tert-butyl ester (50 mg, 0.24 mmol), 2-chloropyrimidine (27 mg, 0.24 mmol), triethylamine (0.1 ml, 0.72 mmol) and THF (2.5 ml) was heated at 180° C. for 10 minutes. The solution was concentrated to afford a solid residue that was dissolved in dichloromethane, which was washed sequentially with sat. aq. sodium bicarbonate and brine, dried (Na$_2$SO$_4$), filtered, and concentrated to afford 50 mg (71%) of the product as a brown solid: $^1$H NMR (400 MHz, CDCl$_3$): δ 8.30 (d, J=12.0 Hz, 2H), 6.52 (t, J=12.0 Hz, 1H), 4.38-4.29 (m, 4H), 3.13 (sb, 2H), 2.42 (m, 2H), 1.69 (q, J=18.0 Hz, 2H), 1.49 (s, 9H); MS (M+1)=291.

(3'-tert-Butyl-biphenyl-4-yl)-(3-Pyrimidin-2-yl-3,8-diaza-bicyclo[3.2.1]oct-8-yl)-methanone A solution of 3-pyrimidin-2-yl-3,8-diaza-bicyclo[3.2.1] octane-8-carboxylic acid tert-butyl ester (64 mg, 0.22 mmol) in HCl/dioxane was stirred for 5 hours at room temperature. The resulting solution was concentrated, and the residue was dissolved in CH$_2$Cl$_2$ (5 mL) and added to a solution of 3'-trifluoromethyl-biphenyl-4-carboxylic acid (117 mg, 0.44 mmol), EDC (85 mg, 0.44 mmol), HOBt (60 mg, 0.44 mol) and TEA (0.1 mL, 0.71 mmol). After stirring overnight, the mixture was treated with EtOAc (50 mL) and water (15 mL). The organic phase was washed with brine (5 mL), dried (MgSO$_4$), filtered, and concentrated under reduced pressure to furnish the crude product. This material was purified by column chromatography (30% EtOAc/hexanes) to give the title compound 14.2 mg, (32%) as a white solid: $^1$H NMR (DMSO): δ 8.35 (d, J=12 Hz, 2H), 7.79-7.76 (m, 3H), 7.68 (dt, J=20, 3 Hz, 1H), 7.63 (d, J=21 Hz, 2H), 7.52-7.43 (m, 2H), 6.62 (t, J=12 Hz, 1H), 4.77 (bs, 1H), 4.41 (d, J=64 Hz, 2H), 4.17 (bs, 1H), 3.14 (bs, 2H), 2.48 (qt, J=5 Hz, 1H), 1.86 (t, J=9 Hz, 2H), 1.60 (d, J=24 Hz, 1H); MS (M+1)=439.

6.19. Human Proline Transporter Assay

The ability of compounds to inhibit the proline transporter was determined as follows. A human SLC6A7 cDNA was cloned into a pcDNA3.1 vector and transfected into COS-1 cells. A cell clone stably expressing proline transporter was selected for the assay.

Transfected cells were seeded at 15,000 cells per well in a 384 well plate and grown overnight. The cells were then washed with Krebs-Ringer's-HEPES-Tris (KRHT) buffer, pH 7.4, containing 120 mM NaCl, 4.7 mM KCl, 2.2 mM CaCl, 1.2 mM MgSO4, 1.2 mM KH$_2$PO$_4$, 10 mM HEPES and 5 mM Tris. The cells were then incubated with 50 μl of KRHT buffer containing 45 nM $^3$H-Proline for 20 minutes at room temperature. Radiolabeled proline uptake was terminated by removing the radiolabeled proline and washing the cells rapidly three times with 100 μl of ice-cold KRHT buffer. Scintillation fluid (50 μl) was added per well, and the amount of tritiated proline present was determined using a Packard Top-Count Scintillation counter.

Nonspecific uptake was determined by measuring of $^3$H-proline uptake in the presence of 2 mM cold proline.

The IC$_{50}$ of a compound was determined by measuring inhibition of four separate samples at ten concentrations, typically beginning with 10 μM followed by nine three-fold dilutions (i.e., 10, 3.3, 1.1, 0.37, 0.12, 0.41, 0.014, 0.0046, 0.0015, and 0 μM). Percent inhibitions were calculated against the control. The $IC_{50}$ of a compound was determined using the ten data points, each of which was an average of the four corresponding measurements.

6.20. Murine Proline Transporter Assay

Forebrain tissue was dissected from a wild type mouse and homogenized in 7 ml ice-cold homogenization buffer: 0.32 M sucrose, 1 mM $NaHCO_3$, protease inhibitor cocktail (Roche).

The brain homogenates were centrifuged at 1000×g for 10 min to remove nuclei. Supernatant was collected and re-centrifuged at 20000×g for 20 min to pellet crude synaptosomes. The synaptosomes were resuspended in ice-cold assay buffer: 122 mM NaCl, 3.1 mM KCl, 25 mM HEPES, 0.4 mM $KH_2PO_4$, 1.2 mM $MgSO_4$, 1.3 mM $CaCl_2$, 10 mM dextrose at pH 7.4. Resuspended synaptosomes were centrifuged again at 20000×g for 20 minutes, and pelleted synaptosomes were resuspended in assay buffer. Protein concentration was measured by DC protein assay kit (BioRad).

Proline transport assay was performed in 100 μl reaction mix consisting of 10 μg synaptosomes, 1 μCi/0.24 μM [H3]-proline in assay buffer for a time between 0 to 20 minutes at room temperature. The reaction was terminated by rapid filtration through GF/B filter plate (Millipore) followed by three rapid washes in 200 ul ice-cold assay buffer. Fifty microliters of Microscint-20 was added to each reaction and incubated for 2 hours. The [H3]-proline transport was determined by radioactivity counting.

To determine proline transport inhibition by compounds, compounds were incubated with the reaction mixture at concentrations ranging from 0 to 10 μM (11 points, beginning at 10 um; 3-fold dilutions; 4 replicates averaged to provide one point). The baseline activity, or nonspecific activity, was measured in the presence of 0.3 mM GGFL (Enkephalin, Sigma) in the reaction. The nonspecific activity was also measured in synaptosomes of SLC6A7 knockout mice. The nonspecific activities measured by the two methods were found to be identical.

6.21. Human Dopamine Transporter Assay

The ability of compounds to inhibit the dopamine transporter was determined as follows. A human DAT cDNA (NM_001044) was cloned into a pcDNA3.1 vector and transfected into COS-1 cells. The resulting cell lines that stably express the dopamine transporter were used for further experimentation.

Transfected cells were seeded at 15,000 cells per well in a 384 well plate and grown overnight. The cells were then washed with Krebs-Ringer's-HEPES-Tris (KRHT) buffer, pH 7.4, containing 125 mM NaCl, 4.8 mM KCl, 1.3 mM $CaCl_2$, 1.2 mM $MgSO_4$ 10 mM D-glucose, 25 mM HEPES, 1 mM sodium ascorbate and 1.2 mM $KH_2PO_4$. The cells were then incubated with 50 μl of KRHT buffer containing 1 μM $^3$H-Dopamine for 10 minutes at room temperature. Radiolabeled dopamine uptake was terminated by removing the radiolabeled dopamine and washing the cells rapidly three times with 100 μl of ice-cold KRHT buffer. Scintillation fluid (50 μl) was added per well and the amount of tritiated dopamine present was determined using a Packard TopCount Scintillation counter.

Nonspecific uptake was determined by measuring of $^3$H-dopamine uptake in the presence of 250 μM benztropine. The $IC_{50}$ of a compound was determined by measuring inhibition of four separate samples at ten concentrations, typically beginning with 10 μM followed by nine three-fold dilutions (i.e., 10, 3.3, 1.1, 0.37, 0.12, 0.41, 0.014, 0.0046, 0.0015, and 0 μM). Percent inhibitions were calculated against the control. The percentage inhibitions were calculated against the control, and the average of the quadruplicates was used for $IC_{50}$ calculation.

6.22. Human Glycine Transporter Assay

The ability of compounds to inhibit the glycine transporter was determined as follows. A human glycine transporter cDNA (NM_006934) was cloned into a pcDNA3.1 vector and transfected into COS-1 cells. The resulting cell lines that stably express the glycine transporter were used for further experimentation.

Transfected cells were seeded at 15,000 cells per well in a 384 well plate and grown overnight. The cells were then washed with Krebs-Ringer's-HEPES-Tris (KRHT) buffer, pH 7.4, containing 120 mM NaCl, 4.7 mM KCl, 2.2 mM $CaCl_2$, 1.2 mM $MgSO_4$, 1.2 mM $KH_2PO_4$, 10 mM HEPES and 5 mM Tris. The cells were then incubated with 50 μl of KRHT buffer containing 166 nM $^3$H-glycine for 10 minutes at room temperature. Radiolabeled glycine uptake was terminated by removing the radiolabeled glycine and washing the cells rapidly three times with 100 μl of ice-cold KRHT buffer. Scintillation fluid (50 μl) was added per well and the amount of tritiated glycine present was determined using a Packard TopCount Scintillation counter.

Nonspecific uptake was determined by measuring $^3$H-glycine uptake in the presence of 2 mM cold glycine. The $IC_{50}$ of a compound was determined by measuring inhibition of four separate samples at ten concentrations, typically beginning with 10 μM followed by nine three-fold dilutions (i.e., 10, 3.3, 1.1, 0.37, 0.12, 0.41, 0.014, 0.0046, 0.0015, and 0 μM). Percent inhibitions were calculated against the control. The percentage inhibitions were calculated against the control, and the average of the quadruplicates was used for $IC_{50}$ calculation.

6.23. Calculating $IC_{50}$ Values

The $IC_{50}$ of a compound with regard to a given target is determined by fitting the relevant data, using the Levenburg Marquardt algorithm, to the equation:

$$y = A + ((B-A)/(1+((C/x)^\wedge D)))$$

wherein A is the minimum y value; B is the maximum y value; C is the $IC_{50}$; and D is the slope. The calculation of the $IC_{50}$ is performed using XLFit4 software (ID Business Solutions Inc., Bridgewater, N.J. 08807) for Microsoft Excel (the above equation is model 205 of that software).

6.24. Pharmacological Effects

A compound having a $PTIC_{50}$ of less than 100 nM was administered to male C57B/6 albino mice subjected to a contextual fear conditioning program using a trace conditioning protocol. The compound was administered at doses ranging from 50-200 mg/kg, and was found to recapitulate phenotypes observed in SLC6A7 KO mice in a dose-dependent manner.

In the protocol, compound was administered p.o., two hours prior to training (Day 1) and again two hours prior to testing the next day (Day 2). Generally, 10-14 mice/group were tested in each study. The two hour pretreatment interval was chosen based on PK results to achieve of peak plasma and brain tissue levels.

Figure 2:
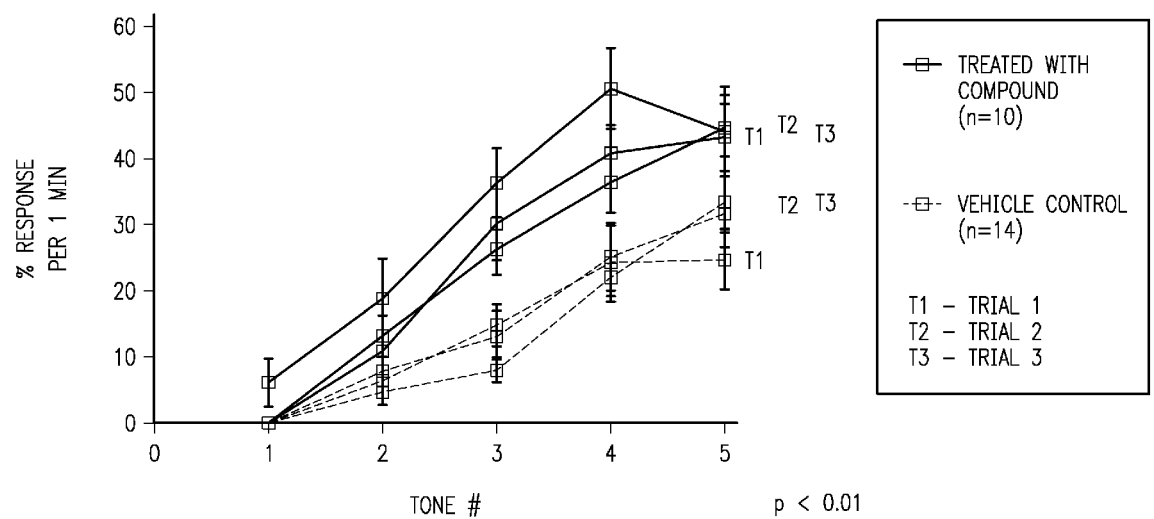
FIG. 2 shows the effect of a compound of the invention administered to mice prior to the learning phase of a conditioned response test.
Figure 3:
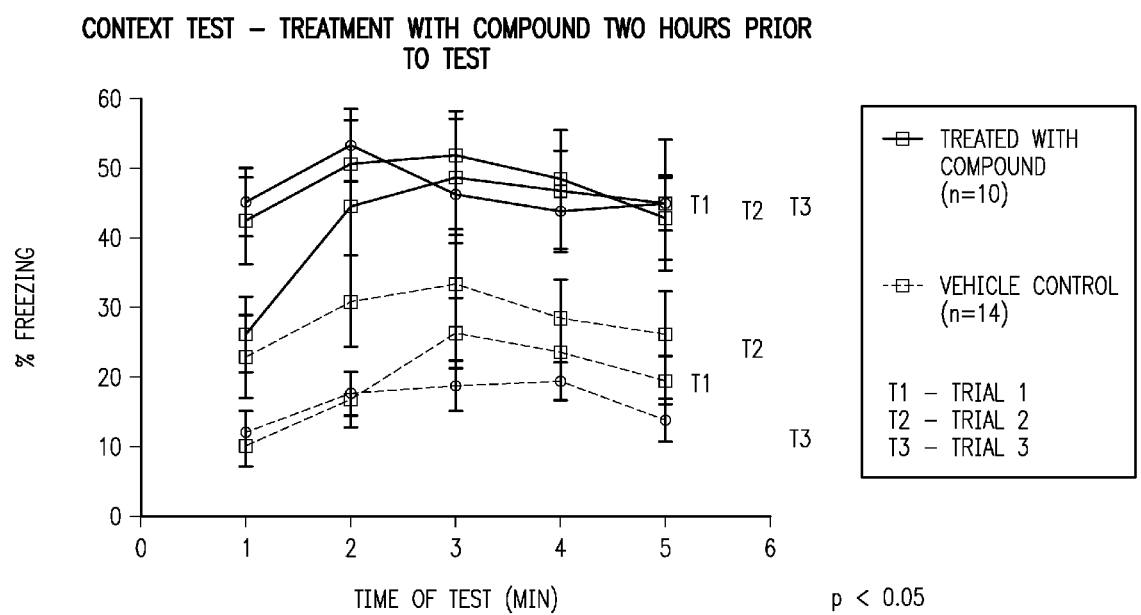
FIG. 3 shows the effect of a compound of the invention administered to mice prior to a context test.

In the trace conditioning experiments, no significant effect was observed in mice dosed at 50 mg/kg, p.o., although a numerical enhancement was seen. But at doses of 100 and 200 mg/kg, p.o., significant increases in performance were observed both during training (Day 1) and testing (Day 2). As shown in FIG. 2, the compound enhanced performance during training as well as during memory testing, indicating that its effects are not changed upon repeated administration. And as shown in FIG. 3, when administered prior to the recall test but not prior to training, the compound enhanced the conditioned response.

In order to gauge whether the compound's effect changed following repeated dosing, it was administered for three days b.i.d. prior to the training day, as well as b.i.d. on the training day and prior to the test. As in the acute studies, the compound was administered two hours prior to the training session and two hours prior to the test session. Based on separate PK studies, this administration regimen was expected to provide blood levels of the compound throughout the study. Results similar to those shown in FIGS. 2 and 3 were observed, suggesting that the compound can enhance both learning and memory/recall.

The compound did not increase freezing by itself in naïve mice, as assessed in an open-field in the conditioning training apparatus, nor in mice given specific conditioning training and then placed in a novel open-field. Therefore, its effects appear to be specific to the learned response, and not due to non-specific enhancement of freezing behavior.

What is claimed is:

1. A compound of the formula

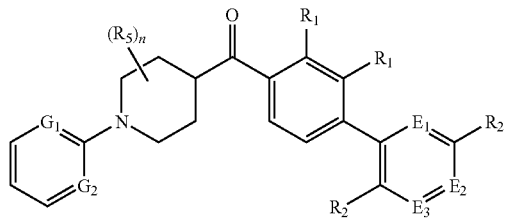

or a pharmaceutically acceptable salt thereof, wherein:
each of $E_1$, $E_2$ and $E_3$ is independently N or $CR_2$;
each of $G_1$ and $G_2$ is independently N or $CR_3$;
each of $R_1$, $R_2$ and $R_3$ is independently hydrogen, halogen, cyano, $R_A$, $OR_A$, $C(O)R_A$, $C(O)OR_A$, $C(O)N(R_AR_B)$, $N(R_AR_B)$, or $SO_2R_A$;
each $R_5$ is independently halogen, cyano, $R_A$, $OR_A$, $C(O)R_A$, $C(O)OR_A$, $C(O)N(R_AR_B)$, $N(R_AR_B)$, or $SO_2R_A$;
each $R_A$ is independently hydrogen or optionally substituted alkyl, aryl, arylalkyl, alkylaryl, heterocycle, heterocycle-alkyl, or alkyl-heterocycle;
each $R_B$ is independently hydrogen or optionally substituted alkyl, aryl, arylalkyl, alkylaryl, heterocycle, heterocycle-alkyl, or alkyl-heterocycle; and
n is 0-5.

2. The compound of claim 1, wherein $G_1$ is N.
3. The compound of claim 1, wherein $G_2$ is N.
4. The compound of claim 1, wherein $G_1$ and $G_2$ are both N.
5. The compound of claim 1, wherein each $R_1$ is hydrogen.
6. The compound of claim 1, wherein $E_1$ is $CR_2$.
7. The compound of claim 1, wherein $E_2$ is $CR_2$.
8. The compound of claim 1, wherein $E_3$ is $CR_2$.
9. The compound of claim 1, wherein $E_1$, $E_2$ and $E_3$ are all $CR_2$.
10. The compound of claim 9, wherein $E_1$, $E_2$ and $E_3$ are all CH.
11. The compound of claim 10, wherein at least one $R_2$ is halo.
12. The compound of claim 11, wherein one of $R_2$ is chloro.
13. The compound of claim 1, wherein n is 0.
14. A compound or a pharmaceutically acceptable salt thereof, wherein the compound is (3'-chlorobiphenyl-4-yl)(1-(pyrimidin-2-yl)piperidin-4-yl)methanone.
15. A pharmaceutical composition comprising a compound of claim 1 and a pharmaceutically acceptable excipient.
16. A capsule or tablet comprising the pharmaceutical composition of claim 15.
17. A pharmaceutical composition comprising a compound of claim 14 and a pharmaceutically acceptable excipient.
18. A capsule or tablet comprising the pharmaceutical composition of claim 17.

* * * * *